US012690828B2

(12) United States Patent
Ide

(10) Patent No.: US 12,690,828 B2
(45) Date of Patent: Jul. 28, 2026

(54) RADIATION DETECTOR, RADIATION DETECTION UNIT, AND RADIATION IMAGING SYSTEM

(71) Applicant: CANON KABUSHIKI KAISHA, Tokyo (JP)

(72) Inventor: Kunihito Ide, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 668 days.

(21) Appl. No.: 18/306,366

(22) Filed: Apr. 25, 2023

(65) Prior Publication Data

US 2023/0371910 A1 Nov. 23, 2023

(30) Foreign Application Priority Data

May 17, 2022 (JP) ................................. 2022-080621
Feb. 8, 2023 (JP) ................................. 2023-017436

(51) Int. Cl.
*A61B 6/42* (2024.01)
*A61B 6/00* (2006.01)

(52) U.S. Cl.
CPC .............. *A61B 6/4208* (2013.01); *A61B 6/44* (2013.01)

(58) Field of Classification Search
CPC ................................. A61B 6/4208; A61B 6/44
See application file for complete search history.

(56) References Cited

U.S. PATENT DOCUMENTS 5,345,107 A * 9/1994 Daikoku .................. F28F 13/00
257/E23.098
11,011,558 B2 5/2021 Sakaguchi et al.

11,417,498 B2 8/2022 Janssen et al.
2015/0260856 A1 * 9/2015 Dierre .................. A61B 6/4208
250/370.09
2023/0375728 A1 * 11/2023 Ide ....................... A61B 6/4208

FOREIGN PATENT DOCUMENTS

CN 101795545 A 8/2010
JP 1-303745 A 12/1989
JP 2-168658 A 6/1990
JP H02168658 A * 6/1990 .......... H01L 23/473
JP 2019087640 A * 6/2019 .......... H01J 37/244
JP 2021018988 A * 2/2021 .............. H01J 37/28

OTHER PUBLICATIONS

Ide, U.S. Appl. No. 18/314,934, filed May 10, 2023.
Official Letter in German Application No. 10 2023 204 139.1 (Jul. 2024).

* cited by examiner

*Primary Examiner* — Uzma Alam
*Assistant Examiner* — Fani Polyzos Boosalis
(74) *Attorney, Agent, or Firm* — Venable LLP

(57) ABSTRACT

A radiation detector includes a semiconductor layer including a light receiving portion configured to receive radiation, and a cooling device disposed at a distance from the semiconductor layer in a direction perpendicular to a main surface of the semiconductor layer. A first member and a second member are provided along a plane that is positioned between the semiconductor layer and the cooling device and that is parallel to the main surface of the semiconductor layer, the second member having physical properties different from physical properties of the first member. In the direction perpendicular to the main surface of the semiconductor layer, the first member and a third member are coupled via a first buffer member, and the second member and the third member are coupled via an adhesive layer.

26 Claims, 24 Drawing Sheets

RADIATION DETECTOR, RADIATION DETECTION UNIT, AND RADIATION IMAGING SYSTEM

BACKGROUND OF THE INVENTION

Field of the Invention

The present invention relates to a radiation detector.

Description of the Related Art

A radiation detector that obtains a radiation image by receiving radiation by a semiconductor element such as a complementary metal oxide semiconductor: CMOS image sensor without using a scintillator, that is, a wavelength conversion element. In such a radiation detector, a semiconductor layer is subjected to thinning because when the radiation enters a deep portion of the semiconductor element, crosstalk occurs or secondary electrons are generated, and therefore the detection precision deteriorates.

Japanese Patent Laid-Open No. 2019-87640 discloses a detector in which the thickness of a semiconductor layer is smaller in at least part of a detection region than in a peripheral region thereof.

Japanese Patent Laid-Open No. 2021-18988 discloses that, when manufacturing a charged particle detector including a sensing layer, a mechanical support layer, and a substrate layer, a step of thinning the substrate layer is performed after coupling the mechanical support layer to an opposite side of the substrate layer with the sensitive layer interposed therebetween.

In addition, in such a radiation detector, the semiconductor element is cooled to suppress generation of a noise.

Japanese Patent Laid-Open No. H02-168658 discloses a cooling device for an electronic device in which a large number of grooves communicating with a space around a heat conducting surface of an electronic device or a cooling body are defined in the heat conducting surface.

Japanese Patent Laid-Open No. H01-303745 discloses a package of a solid-state image sensor coupled to a heat conductor having an excellent thermal conductivity.

When the semiconductor layer of the radiation detector is thinned, occurrence of crosstalk and secondary electrons can be reduced, but the mechanical strength of a semiconductor layer portion is lowered. When manufacturing a radiation detection apparatus, a radiation detector and a cooling device needs to be coupled to each other and attached to the radiation detection apparatus. However, a semiconductor layer portion having low mechanical strength can be damaged in the attachment work, and thus the yield can be lowered. In addition, typically the semiconductor layer portion of the radiation detector has a shorter life time than the radiation detection apparatus because the characteristics of the semiconductor layer portion deteriorate after use for a long period. Therefore, the radiation detector whose characteristics of the semiconductor layer portion have deteriorated needs to be detached and a new radiation detector needs to be attached. However, there is a problem that the semiconductor layer portion having low mechanical strength is easily damaged in the replacement work.

Therefore, there has been desired a technique that can reduce damaging of the semiconductor layer portion that occurs when attaching a radiation detector to a radiation detection apparatus.

SUMMARY OF THE INVENTION

According to a first aspect of the present invention, a radiation detector includes a semiconductor layer including a light receiving portion configured to receive radiation, and a cooling device disposed at a distance from the semiconductor layer in a direction perpendicular to a main surface of the semiconductor layer. A first member and a second member are provided along a plane that is positioned between the semiconductor layer and the cooling device and that is parallel to the main surface of the semiconductor layer, the second member having physical properties different from physical properties of the first member. In the direction perpendicular to the main surface of the semiconductor layer, the first member and a third member are coupled via a first buffer member, and the second member and the third member are coupled via an adhesive layer.

Further features of the present invention will become apparent from the following description of exemplary embodiments with reference to the attached drawings.

DESCRIPTION OF THE EMBODIMENTS

Figure 1A:
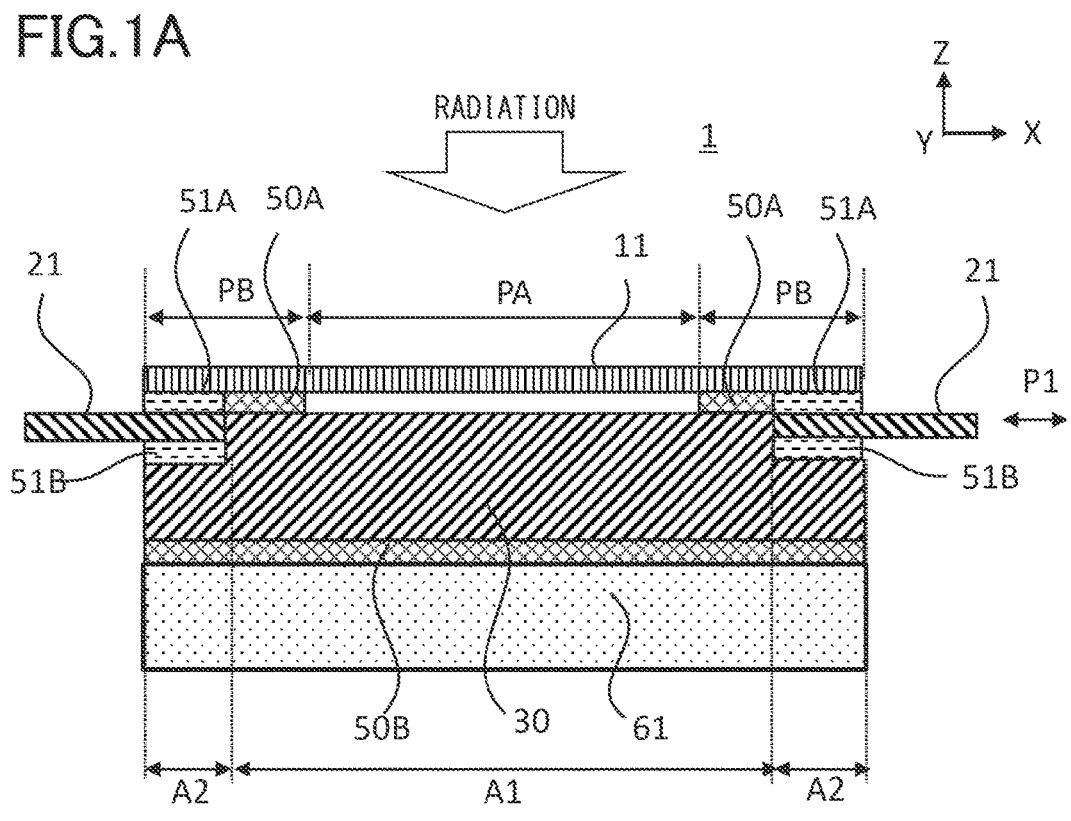
FIG. 1A is a schematic section view of a radiation detector according to a first embodiment.

Embodiments of the present invention will be described with reference to drawings. To be noted, the embodiments described below are merely examples, and for example, details thereof may be appropriately modified for implementation by one skilled in the art within the scope of the present invention.

Elements denoted by the same reference numerals in the drawings referred to in the description of embodiments and examples below have substantially the same functions unless otherwise described. In addition, the drawings do not necessarily match the actual shape, size, and layout because the drawings may be schematically expressed for the sake of convenience of illustration and description.

Radiation detected by a radiation detector according to the embodiments may be an electromagnetic wave or a corpuscular ray. The electromagnetic wave may be light such as infrared light, visible light, or ultraviolet light, an electric wave such as a micro wave, or ionizing radiation such as an X-ray or a gamma ray. Examples of the corpuscular ray include an alpha ray, a beta ray, an electron beam, a neutron beam, a proton beam, a heavy ion beam, and a meson beam. The structure of the radiation detector, for example, the thickness of a semiconductor layer that converts the radiation into an electric signal or the like may be appropriately set in accordance with the transmission characteristics and absorption characteristics of the radiation to be detected.

In the embodiments described below, a cooling device is disposed at a distance from a semiconductor layer in a direction perpendicular to a main surface of the semiconductor layer. A first member and a second member different from the first member in type (physical properties) are provided along a plane (virtual plane) that is positioned between the semiconductor layer and the cooling device and that is parallel to the main surface of the semiconductor layer. In the direction perpendicular to the main surface of the semiconductor layer, the first member and the third member are coupled via a first buffer member, and the second member and the third member are coupled via an adhesive layer.

In a first embodiment that will be described later, a heat conducting member 30 serving as the first member and a circuit board 21 serving as the second member are provided along a plane P1, and a semiconductor layer 11 corresponds to the third member as illustrated in FIGS. 1A to 2C.

In a second embodiment that will be described later, the heat conducting member 30 serving as the first member and the circuit board 21 serving as the second member are provided along a plane P2, and the semiconductor layer 11 corresponds to the third member as illustrated in FIGS. 4A to 5C.

In a third embodiment that will be described later, a heat conducting member 30A serving as the first member and the circuit board 21 serving as the second member are provided along a plane P3, and a heat conducting member 30B corresponds to the third member as illustrated in FIGS. 7A to 8C.

In a fourth embodiment that will be described later, a heat conducting member 30C serving as the first member and the circuit board 21 serving as the second member are provided along a plane P4, and a heat conducting member 30D corresponds to the third member as illustrated in FIGS. 10A to 11C.

In each embodiment, a first buffer member is used for coupling the first member and the third member, an adhesive layer is used for coupling the second member and the third member, and an excessive force locally acting on the semiconductor layer when an external force is applied can be reduced even in the case where the first member and the second member have different physical properties, for example, different elastic moduli. Therefore, in a work of attaching a radiation detector to a radiation detection apparatus or the like, damaging of the semiconductor layer can be suppressed, and the workability, reliability, and yield can be improved.

First Embodiment

Configuration of Radiation Detector

Figure 1B:
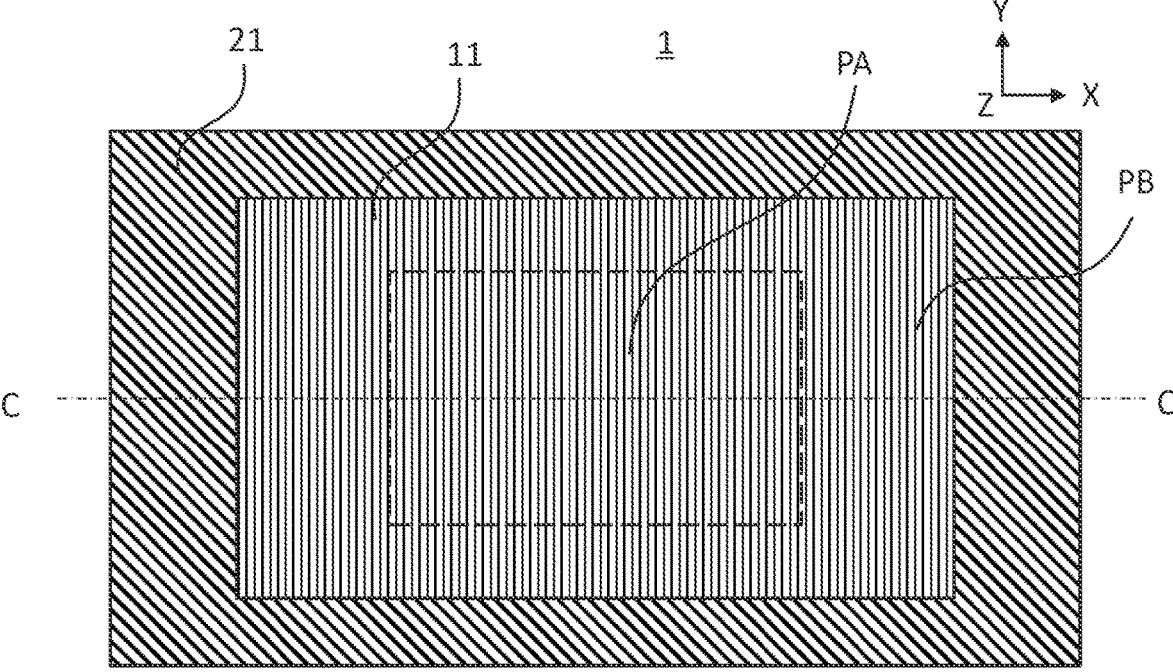
FIG. 1B is a schematic plan view of the radiation detector according to the first embodiment.

FIG. 1B is a plan view of a radiation detector 1 according to the present embodiment as viewed in a radiation incident direction, and FIG. 1A illustrates a cross-section taken along a line C-C in FIG. 1B. The radiation detector 1 includes a semiconductor layer 11, a circuit board 21, a heat conducting member 30, and a cooling device 61. As illustrated in FIG. 1A, the heat conducting member 30 serving as a first member and the circuit board 21 serving as a second member are provided as viewed along the plane P1 parallel to the main surface of the semiconductor layer 11.

The semiconductor layer 11 is constituted by a single crystal layer or polycrystal layer of silicon, germanium, or the like, and includes a detection region PA serving as a light receiving portion and a peripheral region PB. The peripheral region PB has a frame shape surrounding the detection region PA in FIG. 1B, and is a region not included in the detection region PA.

The detection region PA serving as a light receiving portion is a region where a mechanism for converting electrons generated by incident radiation into an output signal is provided, and has a structure in which a plurality of pixels and reading circuits for forming an image based on the radiation are arranged in a matrix shape. The light receiving portion can be also referred to as a region where the radiation is incident, and can be also referred to as a detection portion. The plurality of pixels can each include a photodiode similarly to a CMOS image sensor and a charge-coupled device: CCD. As the photodiode, a compound semiconductor such as cadmium telluride (CdTe) or cadmium zinc telluride (CdZnTe) may be used. In addition, the photon counting principle may be used, and a device such as a single photon avalanche diode may be used.

In the detection region PA, a circuit of a system in which electrons accumulated in a photodiode are transferred to a floating diffusion layer via a transfer transistor and the potential is read via a source follower can be provided similarly to a CMOS image sensor or a CCD. A circuit of a system in which the potential of the accumulating portion is directly used as the gate potential of the source follower without using the transfer transistor may be provided.

In the peripheral region PB, peripheral circuits such as a driving circuit, a control circuit, a signal processing circuit, and an output circuit, an input terminal, and an output terminal are provided. The driving circuit is a circuit that scans and drives a reading circuit of each pixel in the detection region PA. The control circuit is a circuit that controls the driving timing of the driving circuit, the signal processing circuit, and the like, and includes a timing generator and the like. The signal processing circuit processes a signal read out from the reading circuit in the detection region PA, and includes an amplifying circuit, an A/D conversion circuit, and the like. The output circuit converts the signal obtained by the signal processing circuit into a predetermined format, outputs the converted signal, and includes a differential transmission circuit. The input terminal is a terminal through which power, a control signal, and the like are input from the outside, and the output terminal is a terminal through which a signal is output to the outside.

The semiconductor layer 11 may be a substrate having a uniform thickness as illustrated in FIG. 1A, but may be configured such that the thickness of the detection region PA is smaller than the thickness of the peripheral region PB to suppress occurrence of crosstalk and secondary electrons. In this case, a single substrate may be processed such that the thickness of the detection region PA is reduced, or another substrate may be stuck on a peripheral region of a thin substrate such that the thickness of the semiconductor layer is larger in the peripheral region. Alternatively, a configuration in which a plurality of substrates is bonded by a known method and then a thinning process is performed on a portion corresponding to the detection region PA may be employed. For example, in the case of using CdTe or CdZnTe as a photodiode, a configuration in which the signal reading circuit portion is constituted by a CMOS or the like that has been separately produced and the photodiode and the circuit portion are bonded via solder or the like to form the semiconductor layer 11 may be employed. In consideration of the balance between suppressing crosstalk and securing mechanical strength, the thickness of the detection region PA is preferably 10 μm to 100 μm, and more preferably 25 μm to 75 μm. Typically, the thickness of the detection region PA is set to 50 μm.

In the case where a main surface on which the radiation is incident is referred to as a front surface and a main surface opposite thereto is referred to as a back surface in the semiconductor layer 11, the back surface of the detection region PA opposes the heat conducting member 30 with a space therebetween. In addition, in the peripheral region PB, the back surface on the outer edge side in plan view opposes the circuit board 21 with the adhesive layer 51A therebetween. In the peripheral region PB, the back surface on the detection region PA side opposes the heat conducting member 30 with the first buffer member 50A therebetween.

In addition, when viewed in a Z direction that is perpendicular to the main surface of the semiconductor layer 11, a region where the circuit board 21 is not present between the cooling device 61 and the semiconductor layer 11 will be referred to as a region A1, and a region where the circuit board 21 is present between the cooling device 61 and the semiconductor layer 11 will be referred to as a region A2. In at least part of the region A1, the semiconductor layer 11 and the heat conducting member 30 are coupled via the first buffer member 50A. That is, in at least part of the region A1, the back surface of the semiconductor layer 11 is in contact with the first buffer member 50A, and the upper surface of the heat conducting member 30 is in contact with the first buffer member 50A. In the region A2, the semiconductor layer 11 and the circuit board 21 are coupled via the adhesive layer 51A obtained by, for example, curing a resin adhesive. That is, in the region A2, the back surface of the semiconductor layer 11 is in contact with the adhesive layer 51A, and the upper surface of the circuit board 21 is in contact with the adhesive layer 51A. As the adhesive constituting the adhesive layer 51A, various resin adhesives such as a heat curing type, a mixing type, and a UV curing type can be used, but the configuration is not limited to this.

The first buffer member 50A is a member including a material that can be more easily deformed by an external force than the adhesive layer 51A, such as a pseudoplastic fluid, a plastic fluid, a double-sided tape, a die attach film, or an adhesive having a lower elastic modulus than the adhesive layer 51A. The effect of the first buffer member 50A will be described in detail later. For the first buffer member 50A, a material that is more easily deformable by an external force than the adhesive layer 51A is used such that an excessive force does not locally act on the semiconductor layer 11 having low mechanical strength when attaching the radiation detector to the radiation detection apparatus. In addition, the first buffer member 50A preferably has high thermal conductivity to act as a path for dissipating the heat generated in the semiconductor layer 11 to the heat conducting member 30.

Although the first buffer member 50A is disposed only in part of the region A1 where the circuit board 21 is not present between the cooling device 61 and the semiconductor layer 11 in FIG. 1A, the first buffer member 50A may be disposed in the entirety of the region A1. For example, a double-sided tape may be disposed in the entirety of the region A1. This is because this widens the heat conducting path for dissipating the heat generated in the semiconductor layer 11 to the heat conducting member 30.

However, in the case where the first buffer member 50A includes a material that reflects the radiation having passed through the semiconductor layer 11 or discharges secondary particles in response to the irradiation by the radiation, such as a metal like silver, the first buffer member 50A is not disposed on the back surface of the detection region PA. This is for suppressing generation of a noise caused by the reflected radiation or the secondary particles incident on the semiconductor layer 11 from the back surface side.

In addition, in the case of using a pseudoplastic fluid or a plastic fluid such as grease or gel as the first buffer member 50A, it is preferable that a space serving as a deformation margin is provided around the first buffer member 50A such that the first buffer member 50A can deform in the X-Y plane when receiving an external force. Although a space is provided on the detection region PA side of the first buffer member 50A in the example of FIG. 1A, a space (gap) may be provided between the first buffer member 50A and the adhesive layer 51A.

To be noted, although an X-Z section is illustrated in FIG. 1A, it is preferable that the first buffer member 50A is also similarly provided in the Y-Z section. That is, the first buffer member 50A is preferably provided to surround the outer side of the detection region PA in plan view, and a frame-shaped or annular first buffer member 50A surrounding the outer side of the detection region PA in plan view may be provided. Alternatively, a plurality of first buffer members 50A may be arranged at an arbitrary pitch on the outside of the detection region PA in plan view.

In the case of using, as the first buffer member 50A, a member that is more easily deformable by an external force such as an adhesive, double-sided tape, or die attach film having a lower elastic modulus than the adhesive layer 51A, it is preferable that the elastic modulus of the first buffer member 50A is, for example, $\frac{1}{10}$ or less of the elastic modulus of the adhesive layer 51A. For example, in the case where the elastic modulus of the adhesive layer 51A is within a range of 150 MPa to 8000 MPa, the elastic modulus of the first buffer member 50A is preferably 0.1 MPa or more and equal to or less than $\frac{1}{10}$ of the elastic modulus of the adhesive layer 51A.

In the present embodiment, a pseudoplastic fluid is preferably used for the first buffer member 50A. A pseudoplastic fluid is a fluid whose viscosity decreases when force is applied thereto, that is, a fluid whose viscosity coefficient is lower when the velocity gradient is higher. The pseudoplastic fluid has higher fluidity under stronger stress unlike a Bingham fluid or a dilatant fluid. In the present embodiment, a grease that is a pseudoplastic fluid and that is a semi-solid or semi-fluidic lubricant can be preferably used for the first buffer member 50A. Specifically, for example, a grease that has a worked penetration indicating the hardness of the grease of 200 to 385, belongs to a semi-hard to soft group, but is not a fluid at a normal temperature is used. To suppress contamination of the surroundings thereof by evaporation, a grease whose evaporation amount per 24 hours at 200° C. is 1 wt % or less is preferred. Specifically, HIVAC-G, KS-660B, and the like manufactured by Shin-Etsu Chemical Co., Ltd. can be used. For example, in the case of using a grease mixed with fine particles of a material having high thermal conductivity such as silver, the first buffer member 50A is not disposed on the back surface of the detection region PA for the reason described above.

The circuit board 21 is a board on which an electric circuit realizing functions such as supplying a control signal and power to a radiation detection sensor provided in the semiconductor layer 11, processing a signal output from the semiconductor layer 11, storing a signal, transmitting a signal to an external computer or network, and the like is mounted. Although the input terminals and output terminals of the circuit board 21 and the semiconductor layer 11 are electrically interconnected via unillustrated wire bonding, the electrical connection between the circuit board 21 and the semiconductor layer 11 may be established by a method different from wire bonding. The circuit board 21 is stuck on the heat conducting member 30 via the adhesive layer 51B. As the circuit board 21, for example, a multilayer printed wiring board FR-4 is used.

As the substrate of the circuit board 21, for example, glass epoxy resin, paper epoxy resin, glass polyimide resin, or the like is used. The circuit board 21 and the heat conducting member 30 used in the present embodiment are members having different physical properties, and the circuit board 21 can be referred to as a member that is more elastically deformable, that is, a member having a lower elastic modulus than the heat conducting member 30 formed from a hard material.

The heat conducting member 30 is a member for efficiently transmitting the heat of the semiconductor layer 11 and the circuit board 21 to the cooling device 61. For example, a material having high thermal conductivity such as Mo, Cu, CuW, CuMo, Si, SiC, SiN, AlN, Al$_2$O$_3$, or synthesized diamond is preferably used for the heat conducting member 30. A material having a thermal conductivity of 10 [W/mK] or more is used, and particularly, a material having a thermal conductivity of 100 [W/mK] or more is preferably used. Specific examples of this include CuW having a thermal conductivity of 140 to 250 [W/mK], Si having a thermal conductivity of 151 [W/mK], Cu having a thermal conductivity of 394 [W/mK], and Al$_2$O$_3$ having a thermal conductivity of 17 [W/mK], but other materials can be also used. The thickness of the heat conducting member 30 in the Z direction is appropriately set in consideration of the balance between the distance from the semiconductor layer 11 serving as a heat source to the cooling device 61 along a heat transmission path and the mechanical strength needed for the heat conducting member 30. The heat conducting member 30 is a member that has a higher elastic modulus and is less deformable by an external force than the circuit board 21. The heat conducting member 30 is coupled to the cooling device 61 via a second buffer member 50B.

The second buffer member 50B is easily attachable and detachable, has an effect of buffering an external force, and is formed from a material having high thermal conductivity. For example, the second buffer member 50B is a pseudo-plastic fluid, a plastic fluid, a double-sided tape, a die attach film, or the like. This is employed such that an excessive force is not applied to the radiation detection unit when coupling the radiation detection unit to the cooling device 61 disposed on the body side of the radiation detection apparatus after the semiconductor layer 11, the circuit board 21, and the heat conducting member 30 are assembled into a unit. In addition, this is employed for facilitating the separation between the radiation detection unit and the cooling device 61 when the semiconductor layer 11 has deteriorated and the unit needs to be replaced.

The cooling device 61 is, for example, a device capable of heat exchange such as a Peltier device or a liquid-cooling piping. The heat generated by the semiconductor layer 11 and the circuit board 21 is exhausted by the cooling device 61 via the heat conducting member 30. Particularly, as a result of cooling the semiconductor layer 11, dark current of the detection portion serving as a noise is reduced, and therefore highly accurate detection data (radiation image data) can be obtained.

Attachment of Radiation Detector

Figure 2A:
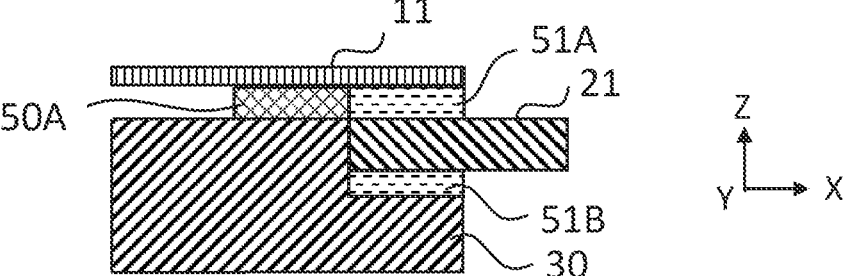
FIG. 2A is a diagram illustrating a unit formation step of the radiation detector according to the first embodiment.

A procedure of attaching the radiation detector according to the present embodiment to the radiation detection apparatus will be described with reference to FIGS. 2A to 2C. In addition, as a first comparative embodiment, an example of coupling the semiconductor layer 11 and the heat conducting member 30 by using only an adhesive layer without using a first buffer member in a region A1 will be described with reference to FIGS. 3A to 3C. To be noted, for the sake of convenience of illustration, only the right end side in FIG. 1A is illustrated in these section views.

Figure 3A:
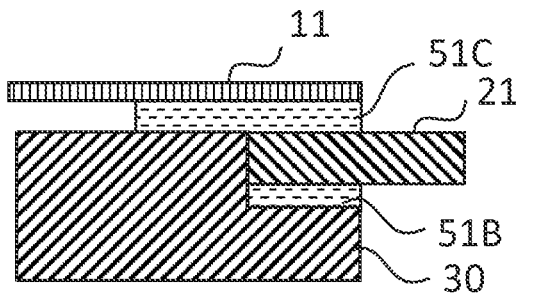
FIG. 3A is a diagram illustrating a unit formation step of a radiation detector according to a first comparative embodiment.
Figure 3A:
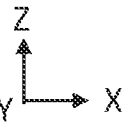

First, the first comparative embodiment will be described. First, as illustrated in FIG. 3A, a unit is formed by coupling the semiconductor layer 11, the circuit board 21, and the heat conducting member 30 by an adhesive layer 51C and an adhesive layer 51B. At this time, each member is positioned by using a jig or the like such that an excessive force is not applied to the semiconductor layer 11, and the radiation detection unit is formed by fixing each member by using an adhesive.

Figure 3B:
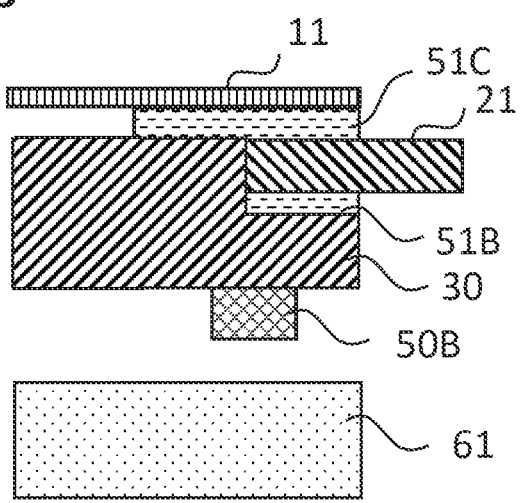
FIG. 3B is an attachment preparation step of the radiation detector according to the first comparative embodiment.
Figure 3B:
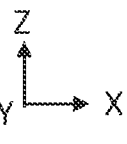

Next, as illustrated in FIG. 3B, the second buffer member 50B (for example, an appropriate amount of grease) is applied on the lower surface of the heat conducting member 30, and alignment in the X and Y directions is performed while the heat conducting member 30 and the cooling device 61 are separated in the Z direction. To be noted, the second buffer member 50B may be applied on the upper surface of the cooling device 61 instead of the lower surface of the heat conducting member 30, or may be applied on both the lower surface of the heat conducting member 30 and the upper surface of the cooling device 61 in some cases.

Figure 3C:
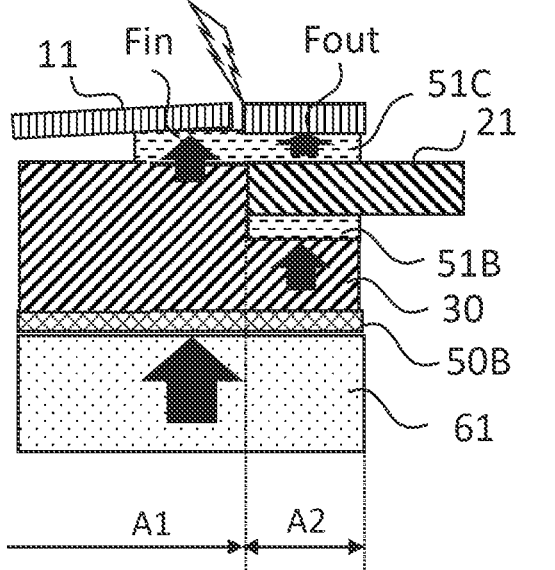
FIG. 3C is a diagram schematically illustrating a force acting when attaching the radiation detector according to the first comparative embodiment.
Figure 3C:
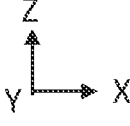

Next, as illustrated in FIG. 3C, the cooling device 61 and the heat conducting member 30 are made closer to each other in the Z direction, and are coupled via the second buffer member 50B. In FIG. 3C, force acting on each portion in this case is schematically indicated by an arrow. Since the heat conducting member 30 has high rigidity, the heat conducting member 30 transmits force of the same magnitude in the Z direction in both the region A1 and the region A2. However, in the region A2, since the circuit board 21 having a lower elastic modulus than the heat conducting member 30 is sandwiched between the adhesive layer 51C and the adhesive layer 51B, and the force in the Z direction is transmitted to the semiconductor layer 11 via these layers, a force Fout applied to the semiconductor layer 11 is smaller than the force of the heat conducting member 30 pressing the adhesive layer 51B. In contrast, in the region A1, the heat conducting member 30 directly presses the adhesive layer 51C in the Z direction, and since the circuit board 21 having a low elastic modulus is not present therebetween, a force Fin acting on the semiconductor layer 11 in the Z direction is remarkably larger than the force Fout. Therefore, excessive stress (resultant force of shearing force, tensile force, and compressive force) locally acts on the semiconductor layer 11 in the vicinity of the boundary between the region A1 and the region A2, and thus the semiconductor layer 11 is easily damaged.

Next, the present embodiment will be described. In the present embodiment, as illustrated in FIG. 2A, first, a unit is formed by coupling the semiconductor layer 11, the circuit board 21, and the heat conducting member 30 by the adhesive layer 51A, the adhesive layer 51B, and the first buffer member 50A. At this time, each member is positioned by using a jig or the like such that an excessive force is not applied to the semiconductor layer 11, and each member is fixed by using the adhesive and buffer member.

Figure 2B:
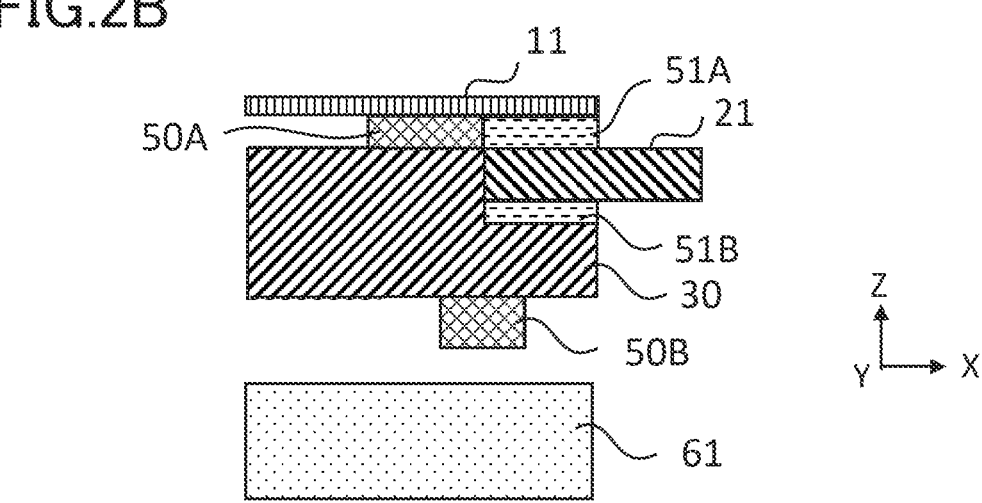
FIG. 2B is an attachment preparation step of the radiation detector according to the first embodiment.

Next, as illustrated in FIG. 2B, for example, an appropriate amount of grease serving as the second buffer member 50B is applied on the lower surface of the heat conducting member 30, and alignment in the X and Y directions is performed while the heat conducting member 30 and the cooling device 61 are separated in the Z direction. To be noted, the second buffer member 50B may be applied on the upper surface of the cooling device 61 instead of the lower surface of the heat conducting member 30, or may be applied on both the lower surface of the heat conducting member 30 and the upper surface of the cooling device 61 in some cases. To be noted, by coupling via the second buffer member 50B, the workability can be improved not only when attaching a radiation detection unit including a semiconductor layer to the cooling device 61 but also when separating an old radiation detection unit from the cooling device 61 to replace the radiation detector.

Figure 2C:
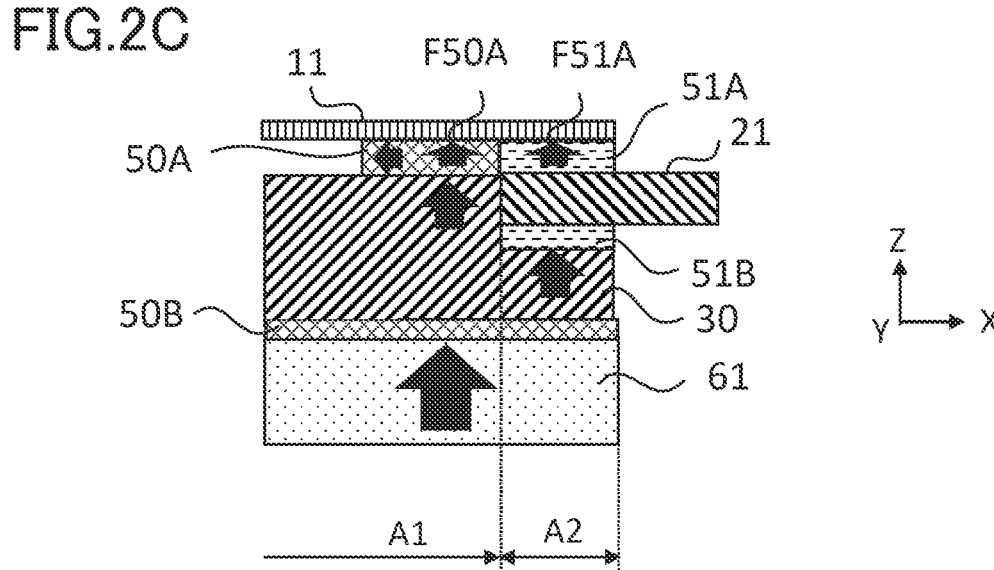
FIG. 2C is a diagram schematically illustrating a force acting when attaching the radiation detector according to the first embodiment.

Next, as illustrated in FIG. 2C, the cooling device 61 and the heat conducting member 30 are made closer to each other in the Z direction, and are coupled via the second buffer member 50B. In FIG. 2C, force acting on each portion in this case is schematically indicated by an arrow. Since the heat conducting member 30 has high rigidity, the heat conducting member 30 transmits force of the same magnitude in the Z direction in both the region A1 and the region A2. However, in the region A2, since the circuit board 21 having a lower elastic modulus than the heat conducting member 30 is sandwiched between the adhesive layer 51A and the adhesive layer 51B, and the force in the Z direction is transmitted to the semiconductor layer 11 via these layers, a force F51A applied to the semiconductor layer 11 is smaller than the force of the heat conducting member 30 pressing the adhesive layer 51B. In contrast, in the region A1, the heat conducting member 30 presses the first buffer member 50A (for example, grease) in the Z direction, and since the first buffer member 50A is formed from an easily deformable material, the first buffer member 50A deforms to spread to an adjacent space in the X-Y plane. Therefore, part of the pressing force from the heat conducting member 30 in the Z direction is used for the deformation of the first buffer member 50A in the horizontal plane, and therefore a force F50A applied from the first buffer member 50A to the semiconductor layer 11 is smaller than the force of the heat conducting member 30 pressing the first buffer member 50A in the Z direction. As a result, the difference in the force in the Z direction acting on the semiconductor layer 11 between the regions A1 and A2 is reduced, and damaging of the semiconductor layer 11 in the vicinity of the boundary between the regions A1 and A2 can be suppressed.

As described above, according to the present embodiment, damaging of the semiconductor layer of the radiation detector can be suppressed when attaching the radiation detector for manufacturing the radiation detection apparatus or when replacing a radiation detector whose characteristics have deteriorated with a new radiation detector.

Second Embodiment

Figures 4A, 4B:
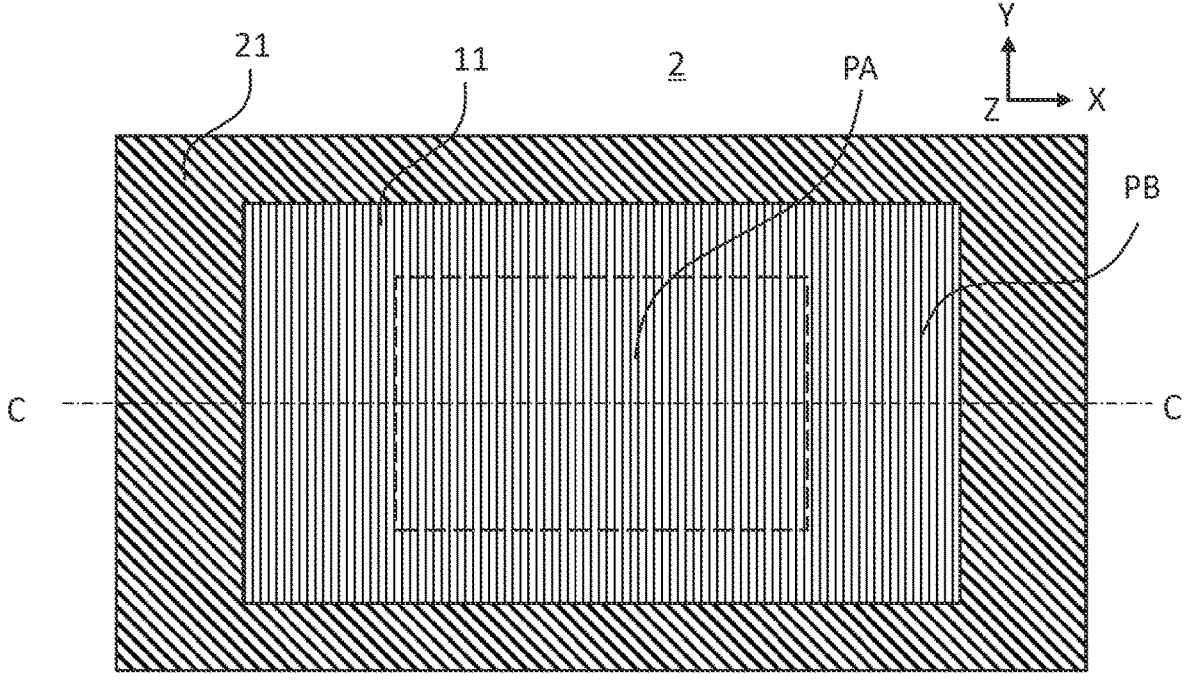
FIG. 4A is a schematic section view of a radiation detector according to a second embodiment.
FIG. 4B is a schematic plan view of the radiation detector according to the second embodiment.

A radiation detector according to a second embodiment will be described. For elements common to the first embodiment, description may be simplified or omitted.
Configuration of Radiation Detector FIG. 4B is a plan view of a radiation detector 2 according to the present embodiment as viewed in a radiation incident direction, and FIG. 4A illustrates a cross-section taken along a line C-C in FIG. 4B. As illustrated in FIG. 4A, the heat conducting member 30 serving as a first member and the circuit board 21 serving as a second member are provided as viewed along a plane P2 parallel to the main surface of the semiconductor layer 11. The radiation detector 2 is the same as the radiation detector 1 of the first embodiment in that the radiation detector 2 includes the semiconductor layer 11, the circuit board 21, the heat conducting member 30, and the cooling device 61, but is different from the radiation detector 1 in that the heat conducting member 30 and the cooling device 61 are not disposed on the back surface side of the detection region PA serving as a light receiving portion. According to the present embodiment, since a space where no member is disposed is provided on the back surface side of the detection region PA, radiation having passed through the semiconductor layer 11 is not reflected in the vicinity of the back surface of the detection region PA or does not cause discharge of secondary particles. Therefore, generation of a noise in the semiconductor layer 11 as a result of an influence from the back surface side can be suppressed. Description of each member is the same as in the first embodiment, and will be therefore omitted.
Attachment of Radiation Detector A procedure of attaching the radiation detector according to the present embodiment to the radiation detection apparatus will be described with reference to FIGS. 5A to 5C. In addition, as a second comparative embodiment, an example of coupling the semiconductor layer 11 and the heat conducting member 30 by using only an adhesive layer without using the first buffer member in the region A1 will be described with reference to FIGS. 6A to 6C. To be noted, for the sake of convenience of illustration, only the right end side in FIG. 4A is illustrated in these section views.

Figure 6A:
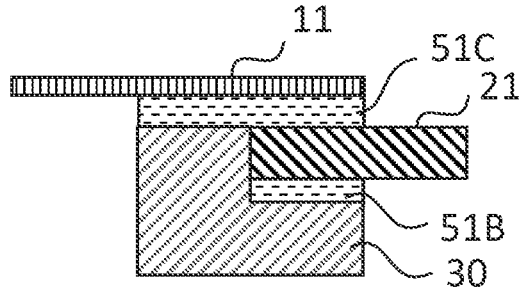
FIG. 6A is a diagram illustrating a unit formation step of a radiation detector according to a second comparative embodiment.
Figure 6A:
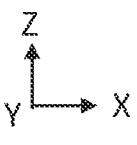

First, the second comparative embodiment will be described. First, as illustrated in FIG. 6A, a unit is formed by coupling the semiconductor layer 11, the circuit board 21, and the heat conducting member 30 by the adhesive layer 51C and the adhesive layer 51B. At this time, each member is positioned by using a jig or the like such that an excessive force is not applied to the semiconductor layer 11, and the radiation detection unit is formed by fixing each member by using an adhesive.

Figure 6B:
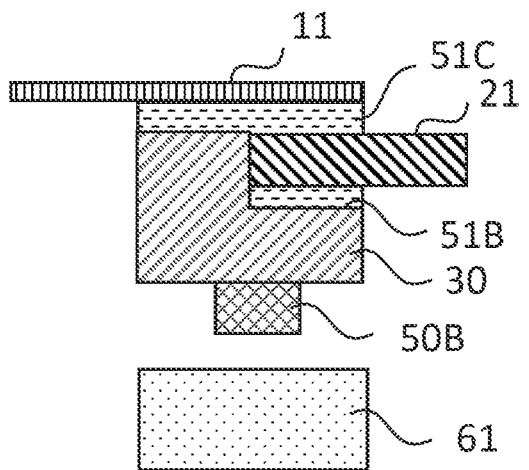
FIG. 6B is an attachment preparation step of the radiation detector according to the second comparative embodiment.
Figure 6B:
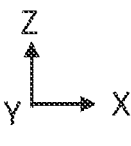

Next, as illustrated in FIG. 6B, the second buffer member 50B (for example, an appropriate amount of grease) is applied on the lower surface of the heat conducting member 30, and alignment in the X and Y directions is performed while the heat conducting member 30 and the cooling device 61 are separated in the Z direction. To be noted, the second buffer member 50B may be applied on the upper surface of the cooling device 61 instead of the lower surface of the heat conducting member 30, or may be applied on both the lower surface of the heat conducting member 30 and the upper surface of the cooling device 61 in some cases.

Figure 6C:
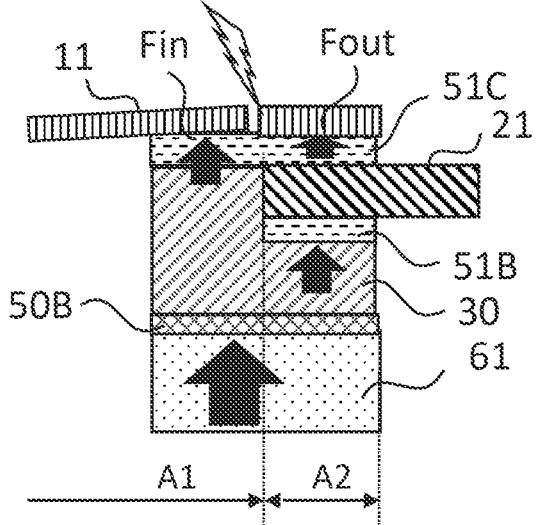
FIG. 6C is a diagram schematically illustrating a force acting when attaching the radiation detector according to the second comparative embodiment.
Figure 6C:
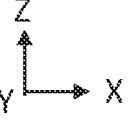

Next, as illustrated in FIG. 6C, the cooling device 61 and the heat conducting member 30 are made closer to each other in the Z direction, and are coupled via the second buffer member 50B. In FIG. 6C, force acting on each portion in this case is schematically indicated by an arrow. Since the heat conducting member 30 has high rigidity, the heat conducting member 30 transmits force of the same magnitude in the Z direction in both the region A1 and the region A2. However, in the region A2, since the circuit board 21 having a lower elastic modulus than the heat conducting member 30 is sandwiched between the adhesive layer 51C and the adhesive layer 51B, and the force in the Z direction is transmitted to the semiconductor layer 11 via these layers, the force Fout applied to the semiconductor layer 11 is smaller than the force of the heat conducting member 30 pressing the adhesive layer 51B. In contrast, in the region A1, the heat conducting member 30 directly presses the adhesive layer 51C in the Z direction, and since the circuit board 21 having a low elastic modulus is not present therebetween, the force Fin acting on the semiconductor layer 11 in the Z direction is remarkably larger than the force Fout. Therefore, excessive stress (resultant force of shearing force, tensile force, and compressive force) locally acts on the semiconductor layer 11 in the vicinity of the boundary between the region A1 and the region A2, and thus the semiconductor layer 11 is easily damaged.

Figure 5A:
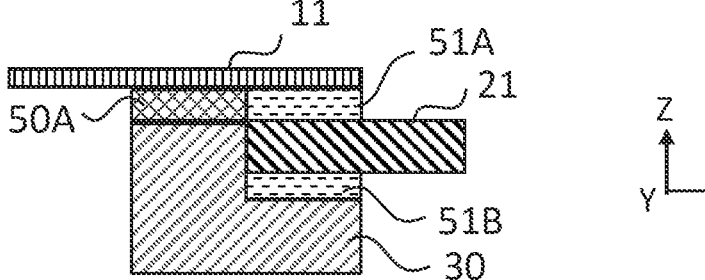
FIG. 5A is a diagram illustrating a unit formation step of the radiation detector according to the second embodiment.

Next, the present embodiment will be described. In the present embodiment, as illustrated in FIG. 5A, a unit is formed by coupling the semiconductor layer 11, the circuit board 21, and the heat conducting member 30 by the adhesive layer 51A, the adhesive layer 51B, and the first buffer member 50A. At this time, each member is positioned by using a jig or the like such that an excessive force is not applied to the semiconductor layer 11, and each member is fixed by using the adhesive and first buffer member.

Figure 5B:
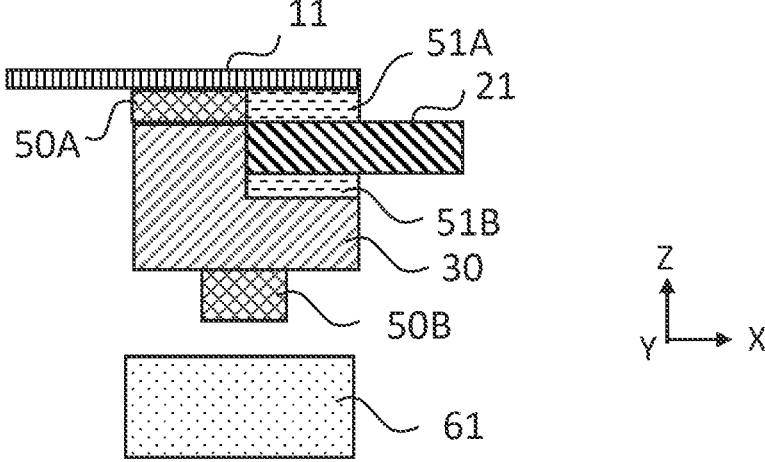
FIG. 5B is an attachment preparation step of the radiation detector according to the second embodiment.

Next, as illustrated in FIG. 5B, the second buffer member 50B (for example, an appropriate amount of grease) is applied on the lower surface of the heat conducting member 30, and alignment in the X and Y directions is performed while the heat conducting member 30 and the cooling device 61 are separated in the Z direction. To be noted, the second buffer member 50B may be applied on the upper surface of the cooling device 61 instead of the lower surface of the heat conducting member 30, or may be applied on both the lower surface of the heat conducting member 30 and the upper surface of the cooling device 61 in some cases. To be noted, by coupling via a second buffer member, the workability can be improved not only when attaching a radiation detection unit including a semiconductor layer to the cooling device 61 but also when separating an old radiation detection unit from the cooling device 61 to replace the radiation detector.

Figure 5C:
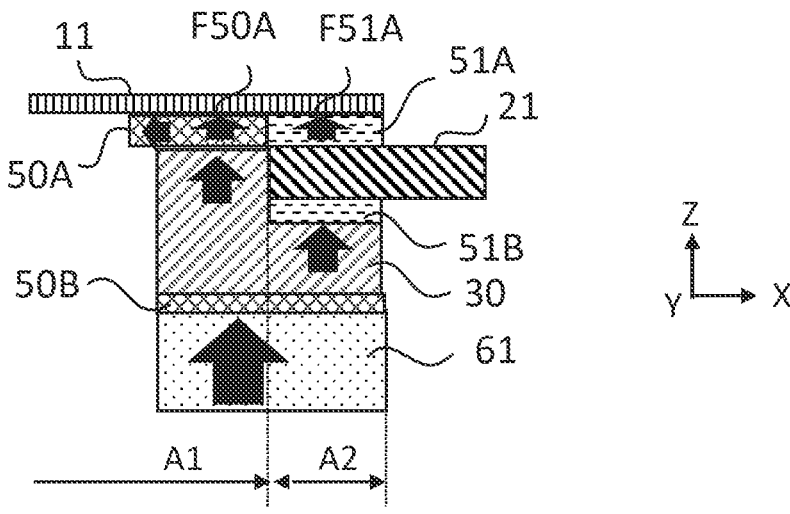
FIG. 5C is a diagram schematically illustrating a force acting when attaching the radiation detector according to the second embodiment.

Next, as illustrated in FIG. 5C, the cooling device 61 and the heat conducting member 30 are made closer to each other in the Z direction, and are coupled via the second buffer member 50B. In FIG. 5C, force acting on each portion in this case is schematically indicated by an arrow. Since the heat conducting member 30 has high rigidity, the heat conducting member 30 transmits force of the same magnitude in the Z direction in both the region A1 and the region A2. However, in the region A2, since the circuit board 21 having a lower elastic modulus than the heat conducting member 30 is sandwiched between the adhesive layer 51A and the adhesive layer 51B, and the force in the Z direction is transmitted to the semiconductor layer 11 via these layers, the force F51A applied to the semiconductor layer 11 is smaller than the force of the heat conducting member 30 pressing the adhesive layer 51B. In contrast, in the region A1, the heat conducting member 30 presses the first buffer member 50A (for example, grease) in the Z direction, and since the first buffer member 50A is formed from an easily deformable material, the first buffer member 50A deforms to spread to an adjacent space in the X-Y plane. Therefore, part of the pressing force from the heat conducting member 30 in the Z direction is used for the deformation of the first buffer member 50A in the X-Y plane, and therefore the force F50A applied from the first buffer member 50A to the semiconductor layer 11 is smaller than the force of the heat conducting member 30 pressing the first buffer member 50A in the Z direction. As a result, the difference in the force in the Z direction acting on the semiconductor layer 11 between the regions A1 and A2 is reduced, and damaging of the semiconductor layer 11 in the vicinity of the boundary between the regions A1 and A2 can be suppressed.

As described above, according to the present embodiment, damaging of the semiconductor layer of the radiation detector can be suppressed when attaching the radiation detector for manufacturing the radiation detection apparatus or when replacing a radiation detector whose characteristics have deteriorated with a new radiation detector.

Third Embodiment

A radiation detector according to a third embodiment will be described. For elements common to the first embodiment, description may be simplified or omitted.

Configuration of Radiation Detector

Figure 7A:
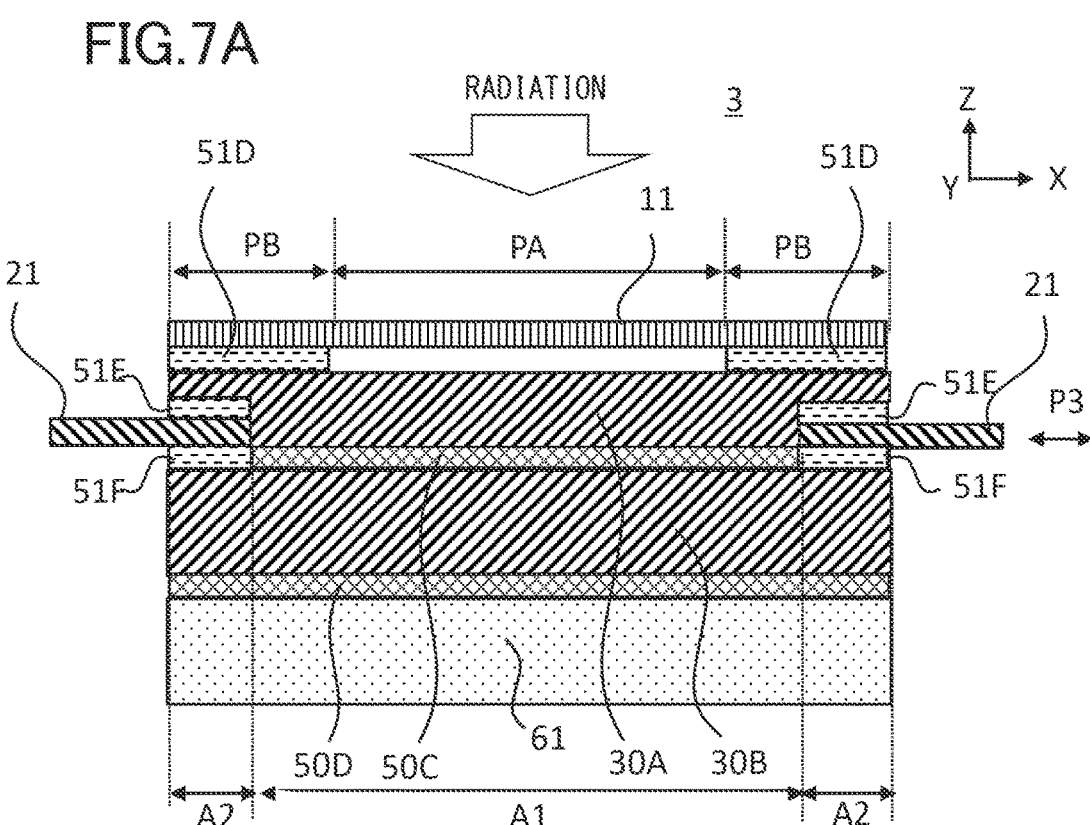
FIG. 7A is a schematic section view of a radiation detector according to a third embodiment.
Figure 7B:
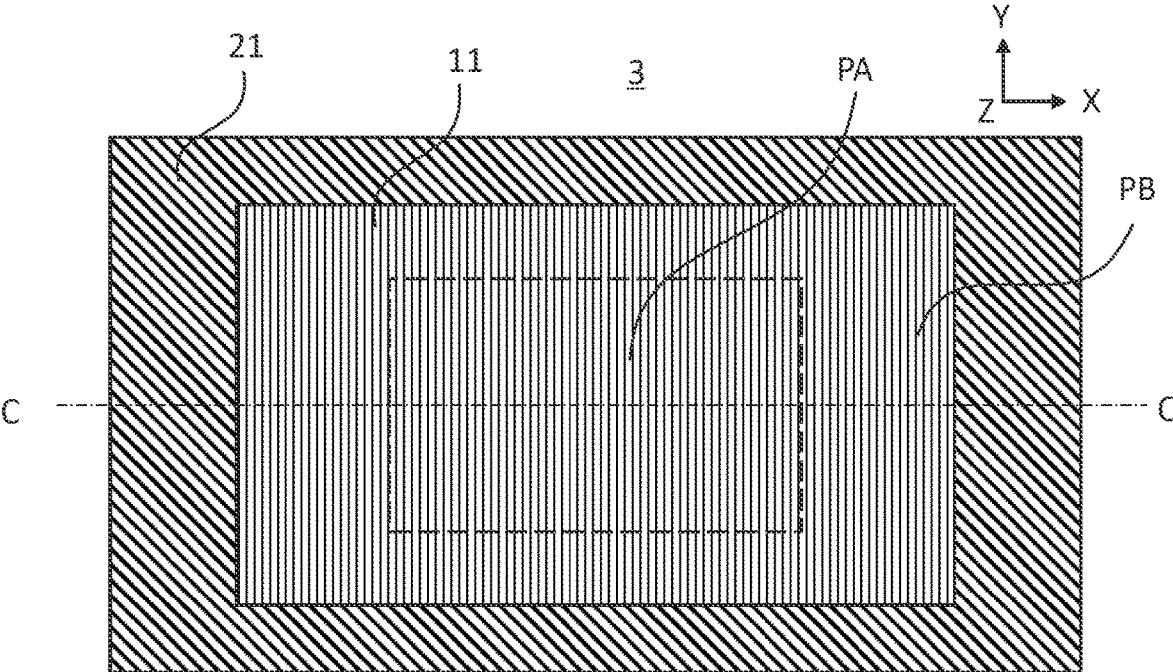
FIG. 7B is a schematic plan view of the radiation detector according to the third embodiment.

FIG. 7B is a plan view of a radiation detector 3 according to the present embodiment as viewed in a radiation incident direction, and FIG. 7A illustrates a cross-section taken along a line C-C in FIG. 7B. The radiation detector 3 includes the semiconductor layer 11, the circuit board 21, a heat conducting member 30A serving as a first heat conducting member, a heat conducting member 30B serving as a second heat conducting member, and the cooling device 61. As illustrated in FIG. 7A, the heat conducting member 30A serving as a first member and the circuit board 21 serving as a second member are provided as viewed along a plane P3 parallel to the main surface of the semiconductor layer 11. Description of the semiconductor layer 11, the circuit board 21, and the cooling device 61 is substantially the same as in the first embodiment, and will be therefore omitted. In addition, description of the materials and physical properties of the adhesive layers and buffer members used in the present embodiment is common to the first embodiment, and will be therefore omitted.

Whereas the radiation detector 1 of the first embodiment includes the single heat conducting member 30, the radiation detector 3 of the present embodiment is different in that the radiation detector 3 includes two of the heat conducting member 30A serving as a first heat conducting member and the heat conducting member 30B serving as a second heat conducting member. In the present embodiment, in the region A2, the semiconductor layer 11 and the heat conducting member 30A are stuck together instead of coupling the semiconductor layer 11 and the circuit board 21 via an adhesive layer, and therefore heat can be efficiently dissipated to the heat conducting member 30A from a peripheral region of the semiconductor layer 11.

Similarly to the description of the first embodiment, when viewed in the Z direction that is perpendicular to the main surface of the semiconductor layer 11, a region where the circuit board 21 is not present between the cooling device 61 and the semiconductor layer 11 will be referred to as a region A1, and a region where the circuit board 21 is present between the cooling device 61 and the semiconductor layer 11 will be referred to as a region A2.

In the case where a main surface on which the radiation is incident is referred to as a front surface and a main surface opposite thereto is referred to as a back surface in the semiconductor layer 11, the back surface of the detection region PA opposes the heat conducting member 30A with a space therebetween. In addition, in a part of the peripheral region PB belonging to the region A1, the semiconductor layer 11, an adhesive layer 51D, the heat conducting member 30A, a first buffer member 50C, the heat conducting member 30B, a second buffer member 50D, and the cooling device 61 are laminated in this order. In addition, in a part of the peripheral region PB belonging to the region A2, the semiconductor layer 11, the adhesive layer 51D, the heat conducting member 30A, an adhesive layer 51E, the circuit board 21, an adhesive layer 51F, the heat conducting member 30B, the second buffer member 50D, and the cooling device 61 are laminated in this order.

Attachment of Radiation Detector

Figure 8A:
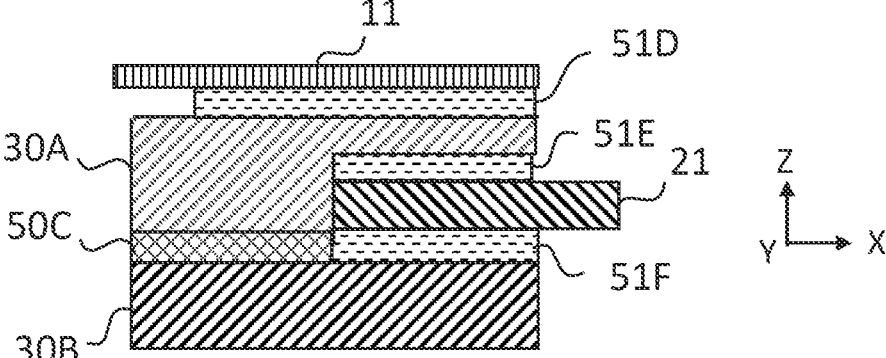
FIG. 8A is a diagram illustrating a unit formation step of the radiation detector according to the third embodiment.

A procedure of attaching the radiation detector according to the present embodiment to the radiation detection apparatus will be described with reference to FIGS. 8A to 8C. In addition, as a third comparative embodiment, an example of coupling the heat conducting member 30A and the heat conducting member 30B by using only the adhesive layer 51F without using the first buffer member 50C in the region A1 will be described with reference to FIGS. 9A to 9C. To be noted, for the sake of convenience of illustration, only the right end side in FIG. 7A is illustrated in these section views.

Figure 9A:
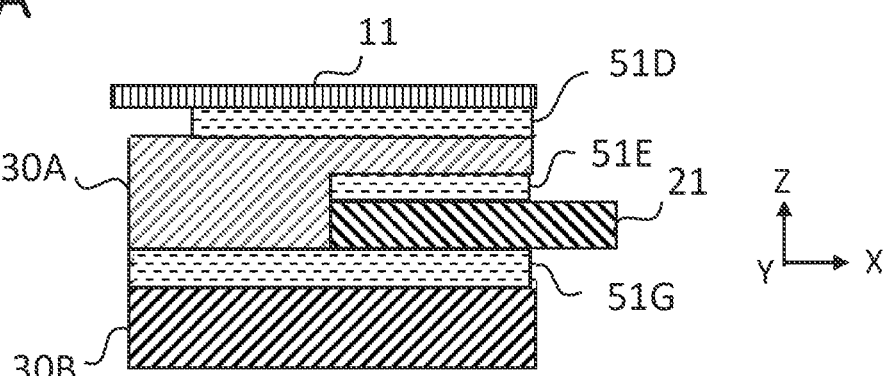
FIG. 9A is a diagram illustrating a unit formation step of a radiation detector according to a third comparative embodiment.

First, the third comparative embodiment will be described. First, as illustrated in FIG. 9A, a unit is formed by coupling the semiconductor layer 11, the circuit board 21, the heat conducting member 30A, and the heat conducting member 30B by the adhesive layer 51D, the adhesive layer 51E, and an adhesive layer 51G. At this time, each member is positioned by using a jig or the like such that an excessive force is not applied to the semiconductor layer 11, and the radiation detection unit is formed by fixing each member by using an adhesive.

Figure 9B:
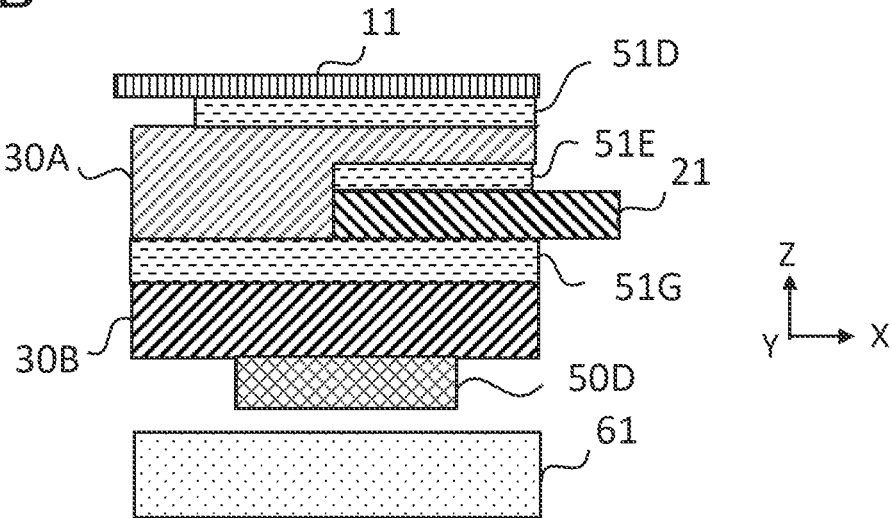
FIG. 9B is an attachment preparation step of the radiation detector according to the third comparative embodiment.

Next, as illustrated in FIG. 9B, the second buffer member 50D (for example, an appropriate amount of grease) is applied on the lower surface of the heat conducting member 30B, and alignment in the X and Y directions is performed while the heat conducting member 30B and the cooling device 61 are separated in the Z direction. To be noted, the second buffer member 50D may be applied on the upper surface of the cooling device 61 instead of the lower surface of the heat conducting member 30B, or may be applied on both the lower surface of the heat conducting member 30B and the upper surface of the cooling device 61 in some cases.

Figure 9C:
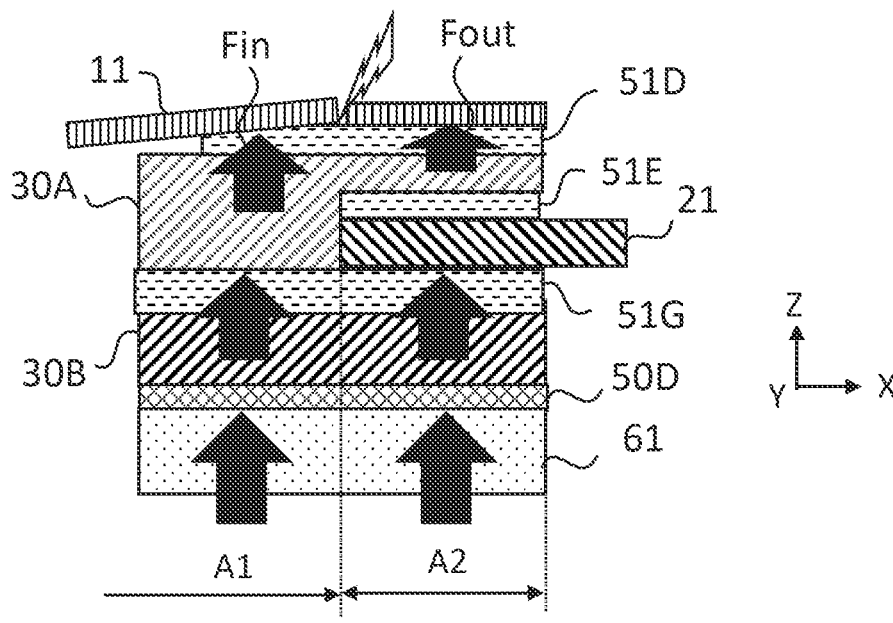
FIG. 9C is a diagram schematically illustrating a force acting when attaching the radiation detector according to the third comparative embodiment.

Next, as illustrated in FIG. 9C, the cooling device 61 and the heat conducting member 30B are made closer to each other in the Z direction, and are coupled via the second buffer member 50D. In FIG. 9C, force acting on each portion in this case is schematically indicated by an arrow. Since the heat conducting member 30B has high rigidity, the heat conducting member 30B transmits force of the same magnitude in the Z direction in both the region A1 and the region A2.

In the region A1, the force in the Z direction is transmitted from the heat conducting member 30B to the heat conducting member 30A via only the adhesive layer 51G. However, in the region A2, the circuit board 21 having a lower elastic modulus than the heat conducting member 30A is sandwiched between the adhesive layer 51G and the adhesive layer 51E, and the force in the Z direction is transmitted from the heat conducting member 30B to the heat conducting member 30A via these layers. Therefore, regarding the force in the Z direction applied to the semiconductor layer 11 from the heat conducting member 30A via the adhesive layer 51D, the force Fin in the region A1 is remarkably larger than the force Fout in the region A2. Therefore, excessive stress (resultant force of shearing force, tensile force, and compressive force) locally acts on the semiconductor layer 11 in the vicinity of the boundary between the region A1 and the region A2, and thus the semiconductor layer 11 is easily damaged.

Next, the present embodiment will be described. In the present embodiment, as illustrated in FIG. 8A, first, a unit is formed by coupling the semiconductor layer 11, the circuit board 21, the heat conducting member 30A, and the heat conducting member 30B by the adhesive layer 51D, the adhesive layer 51E, the adhesive layer 51F, and the first buffer member 50C. At this time, each member is positioned by using a jig or the like such that an excessive force is not applied to the semiconductor layer 11, and each member is fixed by using the adhesive and buffer member.

Figure 8B:
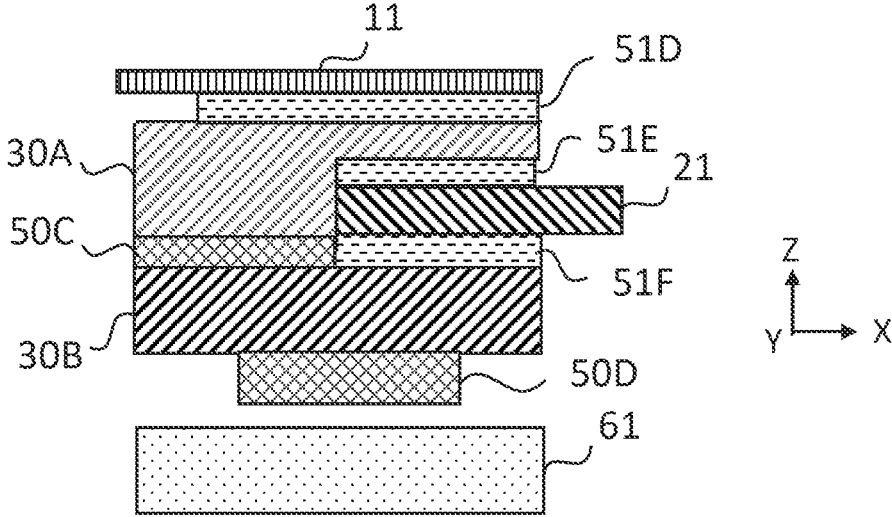
FIG. 8B is an attachment preparation step of the radiation detector according to the third embodiment.

Next, as illustrated in FIG. 8B, the second buffer member 50D (for example, an appropriate amount of grease) is applied on the lower surface of the heat conducting member 30B, and alignment in the X and Y directions is performed while the heat conducting member 30B and the cooling device 61 are separated in the Z direction. To be noted, the second buffer member 50D may be applied on the upper surface of the cooling device 61 instead of the lower surface of the heat conducting member 30B, or may be applied on both the lower surface of the heat conducting member 30B and the upper surface of the cooling device 61 in some cases. To be noted, by coupling via the second buffer member 50D, the workability can be improved not only when attaching a radiation detection unit including a semiconductor layer to the cooling device 61 but also when separating an old radiation detection unit from the cooling device 61 to replace the radiation detector.

Figure 8C:
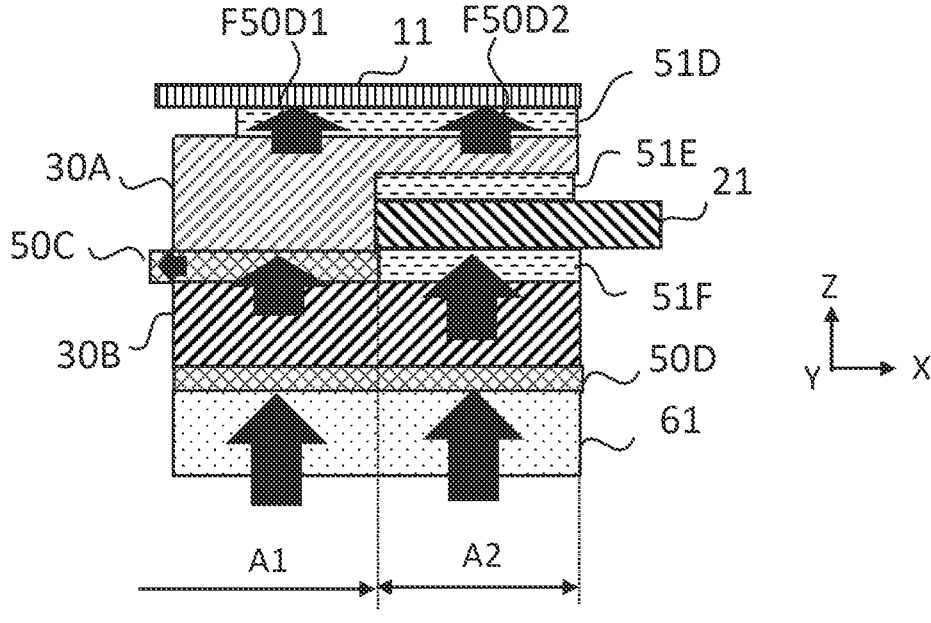
FIG. 8C is a diagram schematically illustrating a force acting when attaching the radiation detector according to the third embodiment.

Next, as illustrated in FIG. 8C, the cooling device 61 and the heat conducting member 30B are made closer to each other in the Z direction, and are coupled via the second buffer member 50D. In FIG. 8C, force acting on each portion in this case is schematically indicated by an arrow. Since the heat conducting member 30B has high rigidity, the heat conducting member 30B transmits force of the same magnitude in the Z direction in both the region A1 and the region A2.

In the region A1, force is transmitted from the heat conducting member 30B to the heat conducting member 30A via the first buffer member 50C, and since the first buffer member 50C is formed from an easily deformable material, the first buffer member 50C deforms to spread to an adjacent space in the X-Y plane. Therefore, part of the pressing force from the heat conducting member 30B in the Z direction is used for the deformation of the first buffer member 50C in the horizontal plane, and therefore the force applied from the first buffer member 50C to the heat conducting member 30A is smaller than the force of the heat conducting member 30B pressing the first buffer member 50C in the Z direction.

In the region A2, the circuit board 21 having a lower elastic modulus than the heat conducting member 30A is sandwiched between the adhesive layer 51F and the adhesive layer 51E, and the force in the Z direction is transmitted from the heat conducting member 30B to the heat conducting member 30A via these layers. Therefore, the force applied from the adhesive layer 51E to the heat conducting member 30A is smaller than the force of the heat conducting member 30B pressing the adhesive layer 51F in the Z direction.

As a result, regarding the force in the Z direction acting on the semiconductor layer 11, the difference between a force F50D1 in the region A1 and a force F50D2 in the region A2 is reduced, and damaging of the semiconductor layer 11 in the vicinity of the boundary between the regions A1 and A2 can be suppressed.

As described above, according to the present embodiment, damaging of the semiconductor layer of the radiation detector can be suppressed when attaching the radiation detector for manufacturing the radiation detection apparatus or when replacing a radiation detector whose characteristics have deteriorated with a new radiation detector.

Fourth Embodiment

A radiation detector according to a fourth embodiment will be described. For elements common to any one of the first to third embodiments, description may be simplified or omitted.

Configuration of Radiation Detector

Figure 10A:
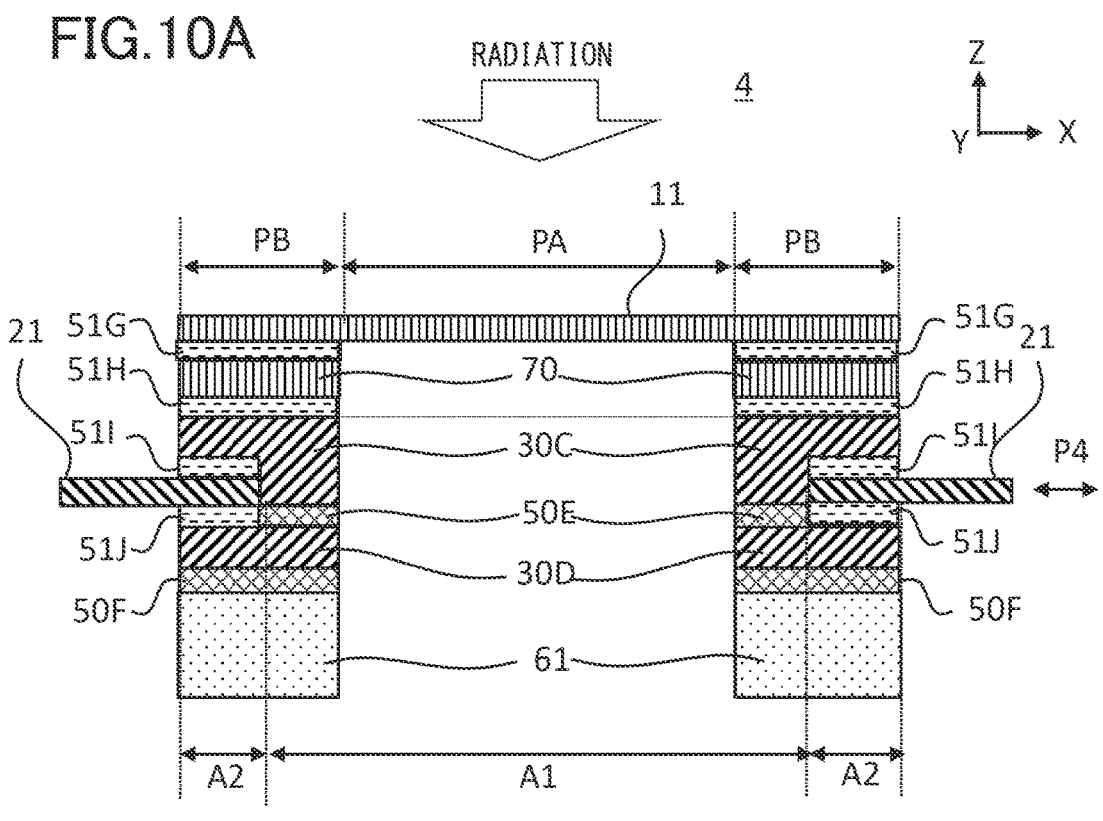
FIG. 10A is a schematic section view of a radiation detector according to a fourth embodiment.
Figure 10B:
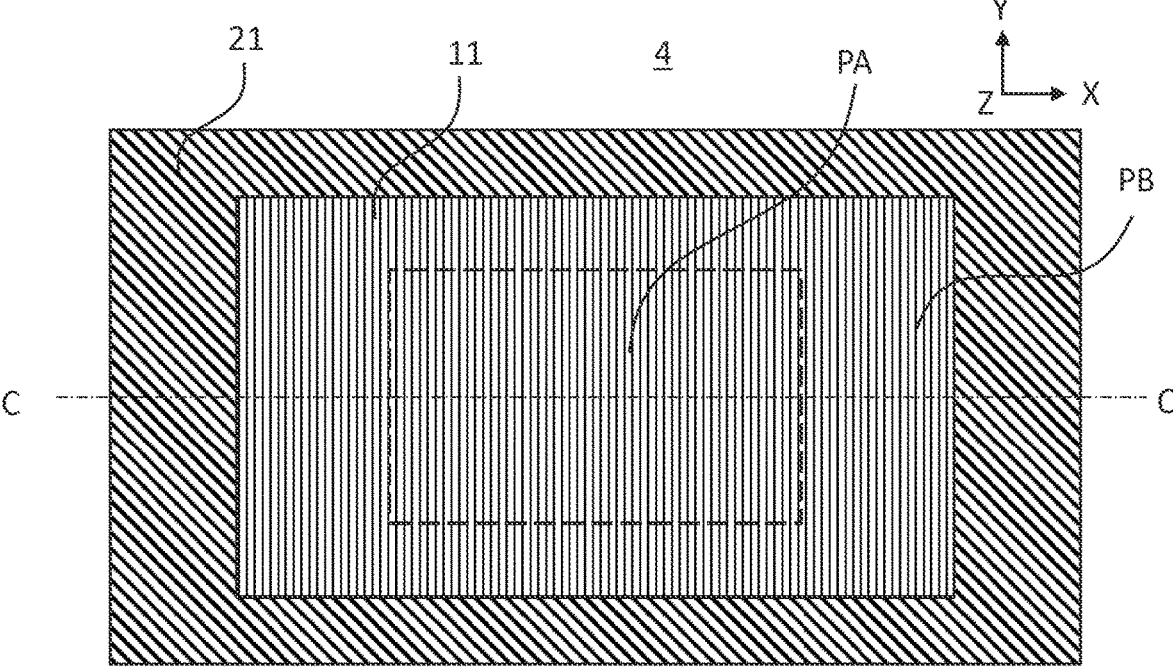
FIG. 10B is a schematic plan view of the radiation detector according to the fourth embodiment.

FIG. 10B is a plan view of a radiation detector 4 according to the present embodiment as viewed in a radiation incident direction, and FIG. 10A illustrates a cross-section taken along a line C-C in FIG. 10B. As illustrated in FIG. 10A, a heat conducting member 30C serving as a first member and the circuit board 21 serving as a second member are provided as viewed along a plane P4 parallel to the main surface of the semiconductor layer 11. The radiation detector 4 includes the semiconductor layer 11, a support member 70, a heat conducting member 30C serving as a first heat conducting member, the circuit board 21, a heat conducting member 30D serving as a second heat conducting member, and the cooling device 61. The present embodiment is the same as the second embodiment in that no heat conducting member or cooling device is disposed on the back surface side of the detection region PA serving as a light receiving portion. That is, also in the present embodiment, since a space where no member is disposed is provided on the back surface side of the detection region PA, radiation having passed through the semiconductor layer 11 is not reflected in the vicinity of the back surface of the detection region PA or does not cause discharge of secondary particles. Therefore, generation of a noise in the semiconductor layer 11 as a result of an influence from the back surface side can be suppressed.

Description of the semiconductor layer 11, the circuit board 21, and the cooling device 61 is substantially the same as in the first embodiment, and will be therefore omitted. In addition, description of the materials and physical properties of the adhesive layers and buffer members used in the present embodiment is common to the first embodiment, and will be therefore omitted. In addition, description of the heat conducting member 30C and the heat conducting member 30D follows the description of the heat conducting member 30A and the heat conducting member 30B in the third embodiment, and will be therefore omitted.

The radiation detector 4 of the present embodiment includes the support member 70 between the semiconductor layer 11 and the heat conducting member 30C serving as a first heat conducting member. The support member 70 can be formed in, for example, a frame shape or a tube shape surrounding the detection region PA in plan view as viewed in a direction perpendicular to the semiconductor layer 11. As the material constituting the support member 70, a material having a line expansion coefficient equal to that of the semiconductor layer 11 or between those of the semiconductor layer 11 and the heat conducting member 30C can be used. In the case where the semiconductor layer 11 and an underlayer member thereof have different thermal expansion coefficients, shape difference occurs when cooling the semiconductor layer 11 by using the cooling device 61, and the semiconductor layer 11 having low mechanical strength can be damaged due to the deformation. In the present embodiment, the support member 70 formed from a material having a line expansion coefficient equal to that of the semiconductor layer 11 or between those of the semiconductor layer 11 and the heat conducting member 30C is interposed between the semiconductor layer 11 and the heat conducting member 30C. As a result of this, the shape difference between the semiconductor layer 11 and the underlayer member is relieved when cooling the semiconductor layer 11, and thus the risk of damaging of the semiconductor layer 11 can be reduced. For example, in the case where the material of the semiconductor layer 11 is silicon and the material of the heat conducting member 30C is CuW, silicon or aluminum nitride is preferably used as the material of the support member 70. That is, the material is selected such that the thermal expansion coefficient of the support member 70 is equal to or higher than the thermal expansion coefficient of the semiconductor layer 11 and lower than the thermal expansion coefficient of the heat conducting member 30C. The support member 70 is preferably thicker than the semiconductor layer 11 so as to have higher mechanical strength than the semiconductor layer 11.

Attachment of Radiation Detector

A procedure of attaching the radiation detector according to the present embodiment to the radiation detection apparatus will be described with reference to FIGS. 11A to 11C. To be noted, for the sake of convenience of illustration, only the right end side in FIG. 10A is illustrated in these section views.

Figure 11A:
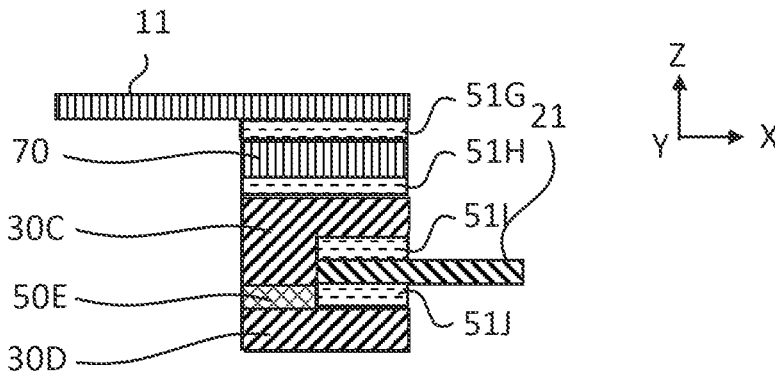
FIG. 11A is a diagram illustrating a unit formation step of the radiation detector according to the fourth embodiment.

In the present embodiment, as illustrated in FIG. 11A, first, a unit is formed by coupling the semiconductor layer 11, the support member 70, the heat conducting member 30C, the circuit board 21, and the heat conducting member 30D by the adhesive layer 51G, an adhesive layer 51H, an adhesive layer 51I, an adhesive layer 51J, and a first buffer member 50E. At this time, each member is positioned by using a jig or the like such that an excessive force is not applied to the semiconductor layer 11, and each member is fixed by using the adhesive and buffer member.

Figure 11B:
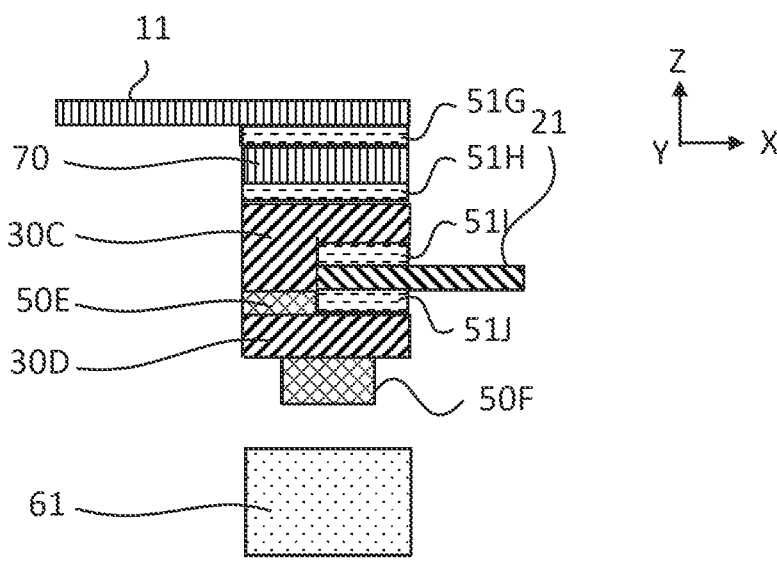
FIG. 11B is an attachment preparation step of the radiation detector according to the fourth embodiment.

Next, as illustrated in FIG. 11B, a second buffer member 50F (for example, an appropriate amount of grease) is applied on the lower surface of the heat conducting member 30D, and alignment in the X and Y directions is performed while the heat conducting member 30D and the cooling device 61 are separated in the Z direction. To be noted, the second buffer member 50F may be applied on the upper surface of the cooling device 61 instead of the lower surface of the heat conducting member 30D, or may be applied on both the lower surface of the heat conducting member 30D and the upper surface of the cooling device 61 in some cases. To be noted, by coupling via the second buffer member 50F, the workability can be improved not only when attaching a radiation detection unit including a semiconductor layer to the cooling device 61 but also when separating an old radiation detection unit from the cooling device 61 to replace the radiation detector.

Figure 11C:
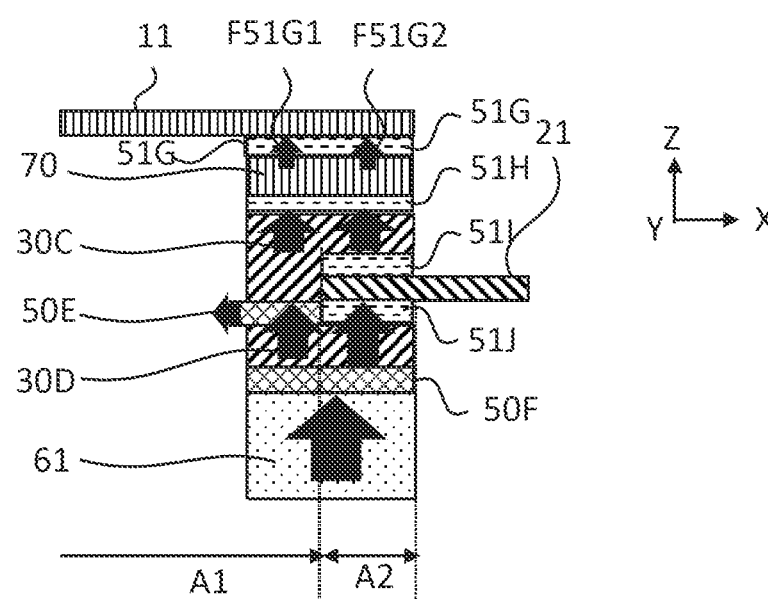
FIG. 11C is a diagram schematically illustrating a force acting when attaching the radiation detector according to the fourth embodiment.

Next, as illustrated in FIG. 11C, the cooling device 61 and the heat conducting member 30D are made closer to each other in the Z direction, and are coupled via the second buffer member 50F. In FIG. 11C, force acting on each portion in this case is schematically indicated by an arrow. Since the heat conducting member 30D has high rigidity, the heat conducting member 30D transmits force of the same magnitude in the Z direction in both the region A1 and the region A2.

In the region A1, force is transmitted from the heat conducting member 30D to the heat conducting member 30C via the first buffer member 50E, and since the first buffer member 50E is formed from an easily deformable material, the first buffer member 50E deforms to spread to an adjacent space in the X-Y plane. Therefore, part of the pressing force from the heat conducting member 30D in the Z direction is used for the deformation of the first buffer member 50E in the horizontal plane, and therefore the force applied from the first buffer member 50E to the heat conducting member 30C is smaller than the force of the heat conducting member 30D pressing the first buffer member 50E in the Z direction.

In the region A2, the circuit board 21 having a lower elastic modulus than the heat conducting member 30C is sandwiched between the adhesive layer 51J and the adhesive layer 51I, and the force in the Z direction is transmitted from the heat conducting member 30D to the heat conducting member 30C via these layers. Therefore, the force applied from the adhesive layer 51I to the heat conducting member 30C is smaller than the force of the heat conducting member 30D pressing the adhesive layer 51J in the Z direction.

As a result, regarding the force in the Z direction acting on the semiconductor layer 11 via the support member 70 and the adhesive layer 51G, the difference between a force F51G1 in the region A1 and a force F51G2 in the region A2 is reduced, and damaging of the semiconductor layer 11 in the vicinity of the boundary between the regions A1 and A2 can be suppressed.

As described above, according to the present embodiment, damaging of the semiconductor layer of the radiation detector can be suppressed when attaching the radiation detector for manufacturing the radiation detection apparatus or when replacing a radiation detector whose characteristics have deteriorated with a new radiation detector.

Fifth Embodiment

A radiation detector according to a fifth embodiment will be described. For elements common to the first embodiment, description may be simplified or omitted.

Configuration of Radiation Detector

Figure 14A:
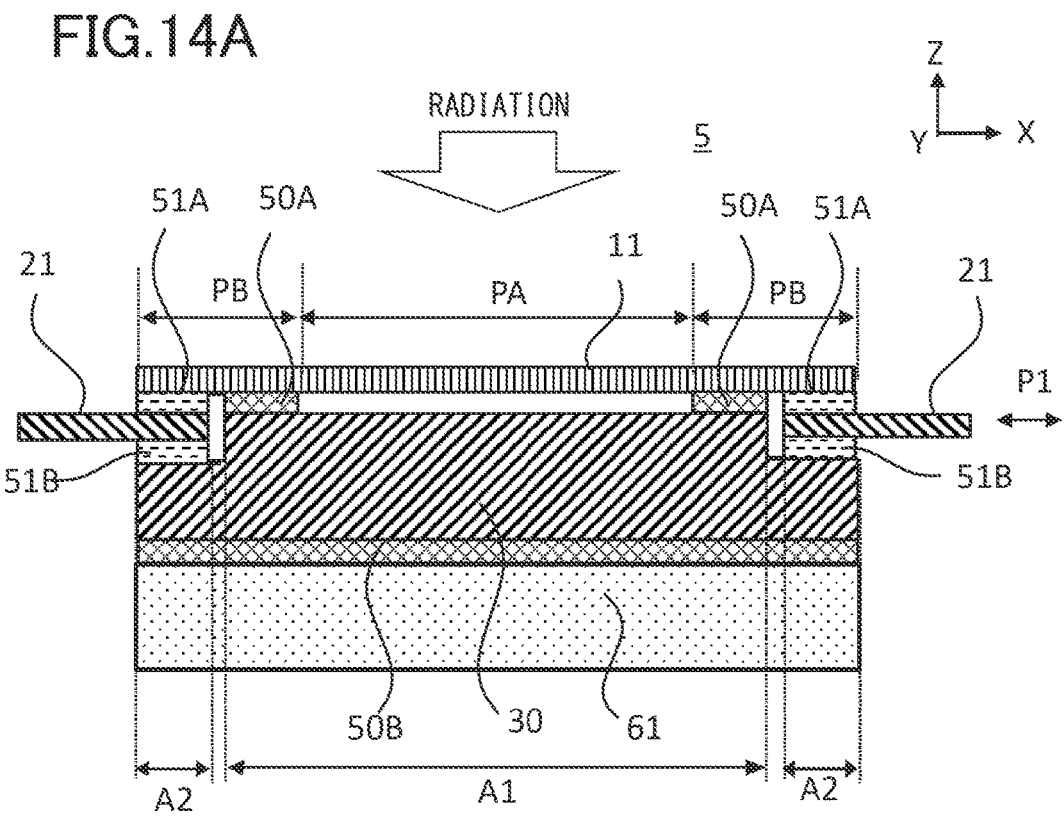
FIG. 14A is a schematic section view of a radiation detector according to a fifth embodiment.
Figure 14B:
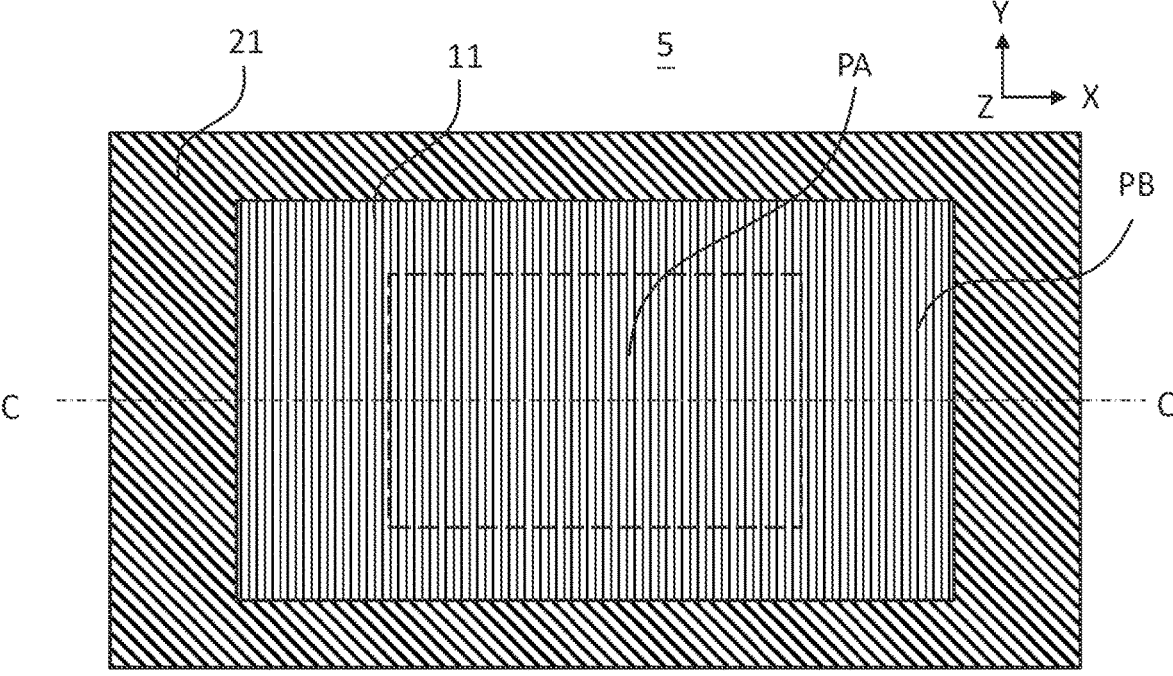
FIG. 14B is a schematic plan view of the radiation detector according to the fifth embodiment.

FIG. 14B is a plan view of a radiation detector 5 according to the present embodiment as viewed in a radiation incident direction, and FIG. 14A illustrates a cross-section taken along a line C-C in FIG. 14B. As illustrated in FIG. 14A, the heat conducting member 30 serving as a first member and the circuit board 21 serving as a second member are provided as viewed along the plane P1 parallel to the main surface of the semiconductor layer 11. The radiation detector 5 is the same as the radiation detector 1 of the first embodiment in that the radiation detector 5 includes the semiconductor layer 11, the circuit board 21, the heat conducting member 30, and the cooling device 61, but is different from the radiation detector 1 in that a space is provided between the adhesive layer 51A and the first buffer member 50A and between the heat conducting member 30 and the circuit board 21. The radiation detector 5 is also different in that a space is provided between a protrusion of the heat conducting member 30 and the adhesive layer 51B, but this space does not have to be provided. According to the present embodiment, since a space where no member is disposed is provided on the back surface side of the detection region PA, radiation having passed through the semiconductor layer 11 is not reflected in the vicinity of the back surface of the detection region PA or does not cause discharge of secondary particles. Therefore, generation of a noise in the semiconductor layer 11 as a result of an influence from the back surface side can be suppressed. Description of each member is the same as in the first embodiment, and will be therefore omitted.

Attachment of Radiation Detector

Figure 15A:
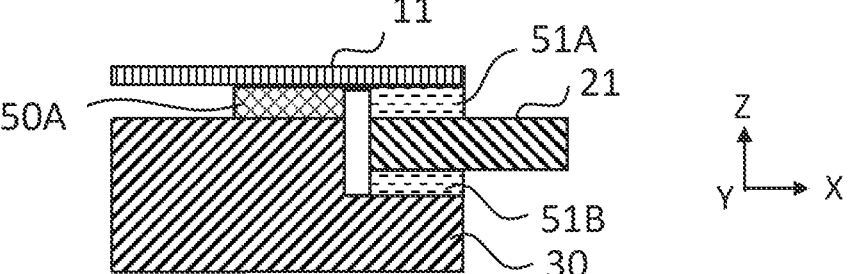
FIG. 15A is a diagram illustrating a unit formation step of the radiation detector according to the fifth embodiment.

A procedure of attaching the radiation detector according to the present embodiment to the radiation detection apparatus will be described with reference to FIGS. 15A to 15C. In addition, as a fourth comparative embodiment, an example of coupling the semiconductor layer 11 and the heat conducting member 30 by using only an adhesive layer without using a first buffer member in the region A1 will be described with reference to FIGS. 16A to 16C. To be noted, for the sake of convenience of illustration, only the right end side in FIG. 14A are illustrated in these section views.

Figure 16A:
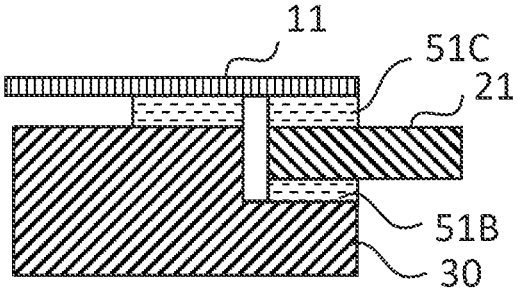
FIG. 16A is a diagram illustrating a unit formation step of a radiation detector according to a fourth comparative embodiment.
Figure 16A:
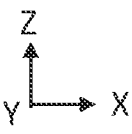

First, the fourth comparative embodiment will be described. First, as illustrated in FIG. 16A, a unit is formed by coupling the semiconductor layer 11, the circuit board 21, and the heat conducting member 30 by the adhesive layer 51C and the adhesive layer 51B. At this time, each member is positioned by using a jig or the like such that an excessive force is not applied to the semiconductor layer 11, and the radiation detection unit is formed by fixing each member by using an adhesive.

Figure 16B:
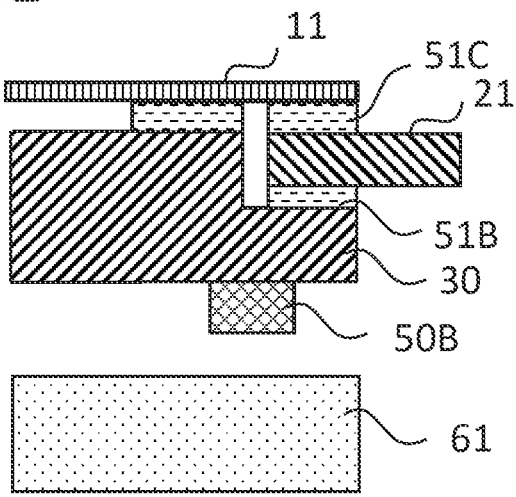
FIG. 16B is an attachment preparation step of the radiation detector according to the fourth comparative embodiment.
Figure 16B:
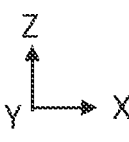

Next, as illustrated in FIG. 16B, the second buffer member 50B (for example, an appropriate amount of grease) is applied on the lower surface of the heat conducting member 30, and alignment in the X and Y directions is performed while the heat conducting member 30 and the cooling device 61 are separated in the Z direction. To be noted, the second buffer member 50B may be applied on the upper surface of the cooling device 61 instead of the lower surface of the heat conducting member 30, or may be applied on both the lower surface of the heat conducting member 30 and the upper surface of the cooling device 61 in some cases.

Figure 16C:
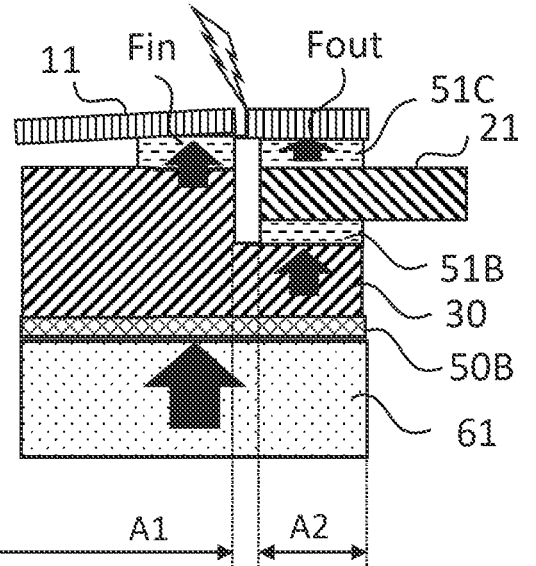
FIG. 16C is a diagram schematically illustrating a force acting when attaching the radiation detector according to the fourth comparative embodiment.
Figure 16C:
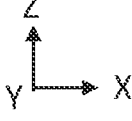

Next, as illustrated in FIG. 16C, the cooling device 61 and the heat conducting member 30 are made closer to each other in the Z direction, and are coupled via the second buffer member 50B. In FIG. 16C, force acting on each portion in this case is schematically indicated by an arrow. Since the heat conducting member 30 has high rigidity, the heat conducting member 30 transmits force of the same magnitude in the Z direction in both the region A1 and the region A2. However, in the region A2, since the circuit board 21 having a lower elastic modulus than the heat conducting member 30 is sandwiched between the adhesive layer 51C and the adhesive layer 51B, and the force in the Z direction is transmitted to the semiconductor layer 11 via these layers, the force Fout applied to the semiconductor layer 11 is smaller than the force of the heat conducting member 30 pressing the adhesive layer 51B. In contrast, in the region A1, the heat conducting member 30 directly presses the adhesive layer 51C in the Z direction, and since the circuit board 21 having a low elastic modulus is not present therebetween, the force Fin acting on the semiconductor layer 11 in the Z direction is remarkably larger than the force Fout. Therefore, excessive stress (resultant force of shearing force, tensile force, and compressive force) locally acts on the semiconductor layer 11 in the vicinity of the boundary between the region A1 and the region A2, and thus the semiconductor layer 11 is easily damaged.

Next, the present embodiment will be described. In the present embodiment, as illustrated in FIG. 15A, a unit is formed by coupling the semiconductor layer 11, the circuit board 21, and the heat conducting member 30 by the adhesive layer 51A, the adhesive layer 51B, and the first buffer member 50A. At this time, each member is positioned by using a jig or the like such that an excessive force is not applied to the semiconductor layer 11, and each member is fixed by using the adhesive and first buffer member.

Figure 15B:
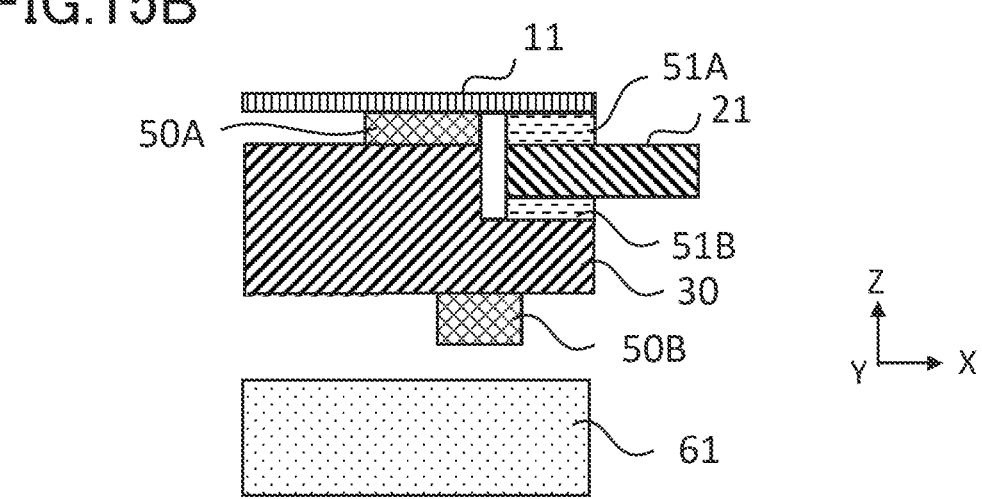
FIG. 15B is an attachment preparation step of the radiation detector according to the fifth embodiment.

Next, as illustrated in FIG. 15B, the second buffer member 50B (for example, an appropriate amount of grease) is applied on the lower surface of the heat conducting member 30, and alignment in the X and Y directions is performed while the heat conducting member 30 and the cooling device 61 are separated in the Z direction. To be noted, the second buffer member 50B may be applied on the upper surface of the cooling device 61 instead of the lower surface of the heat conducting member 30, or may be applied on both the lower surface of the heat conducting member 30 and the upper surface of the cooling device 61 in some cases. To be noted, by coupling via a second buffer member 50B, the workability can be improved not only when attaching a radiation detection unit including a semiconductor layer to the cooling device 61 but also when separating an old radiation detection unit from the cooling device 61 to replace the radiation detector.

Figure 15C:
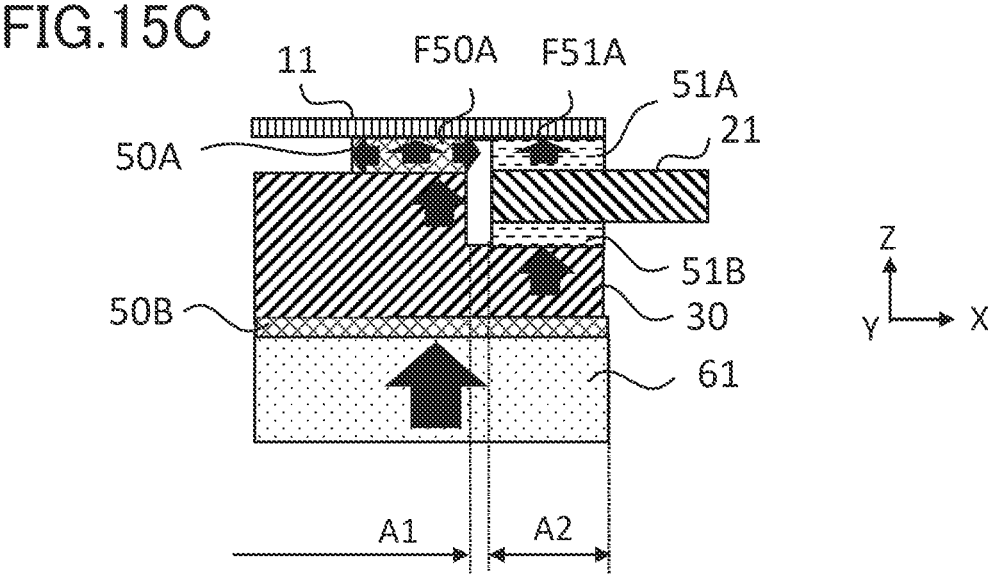
FIG. 15C is a diagram schematically illustrating a force acting when attaching the radiation detector according to the fifth embodiment.

Next, as illustrated in FIG. 15C, the cooling device 61 and the heat conducting member 30 are made closer to each other in the Z direction, and are coupled via the second buffer member 50B. In FIG. 15C, force acting on each portion in this case is schematically indicated by an arrow. Since the heat conducting member 30 has high rigidity, the heat conducting member 30 transmits force of the same magnitude in the Z direction in both the region A1 and the region A2. However, in the region A2, since the circuit board 21 having a lower elastic modulus than the heat conducting member 30 is sandwiched between the adhesive layer 51A and the adhesive layer 51B, and the force in the Z direction is transmitted to the semiconductor layer 11 via these layers, the force F51A applied to the semiconductor layer 11 is smaller than the force of the heat conducting member 30 pressing the adhesive layer 51B. In contrast, in the region A1, the heat conducting member 30 presses the first buffer member 50A (for example, grease) in the Z direction, and since the first buffer member 50A is formed from an easily deformable material, the first buffer member 50A deforms to spread to an adjacent space in the X-Y plane. Therefore, part of the pressing force from the heat conducting member 30 in the Z direction is used for the deformation of the first buffer member 50A in the X-Y plane, and therefore the force F50A applied from the first buffer member 50A to the semiconductor layer 11 is smaller than the force of the heat conducting member 30 pressing the first buffer member 50A in the Z direction. In addition, since there is a space between the adhesive layer 51A and the first buffer member 50A, the first buffer member 50A spreads to the space, and therefore the force is further reduced. Further, the first buffer member 50A can further spread to the space between the adhesive layer 51B and the heat conducting member 30, and therefore the force is further reduced. As a result, the difference in the force in the Z direction acting on the semiconductor layer 11 between the regions A1 and A2 is reduced, and damaging of the semiconductor layer 11 in the vicinity of the boundary between the regions A1 and A2 can be suppressed.

As described above, according to the present embodiment, damaging of the semiconductor layer of the radiation detector can be suppressed when attaching the radiation detector for manufacturing the radiation detection apparatus or when replacing a radiation detector whose characteristics have deteriorated with a new radiation detector.

Sixth Embodiment

Figure 17A:
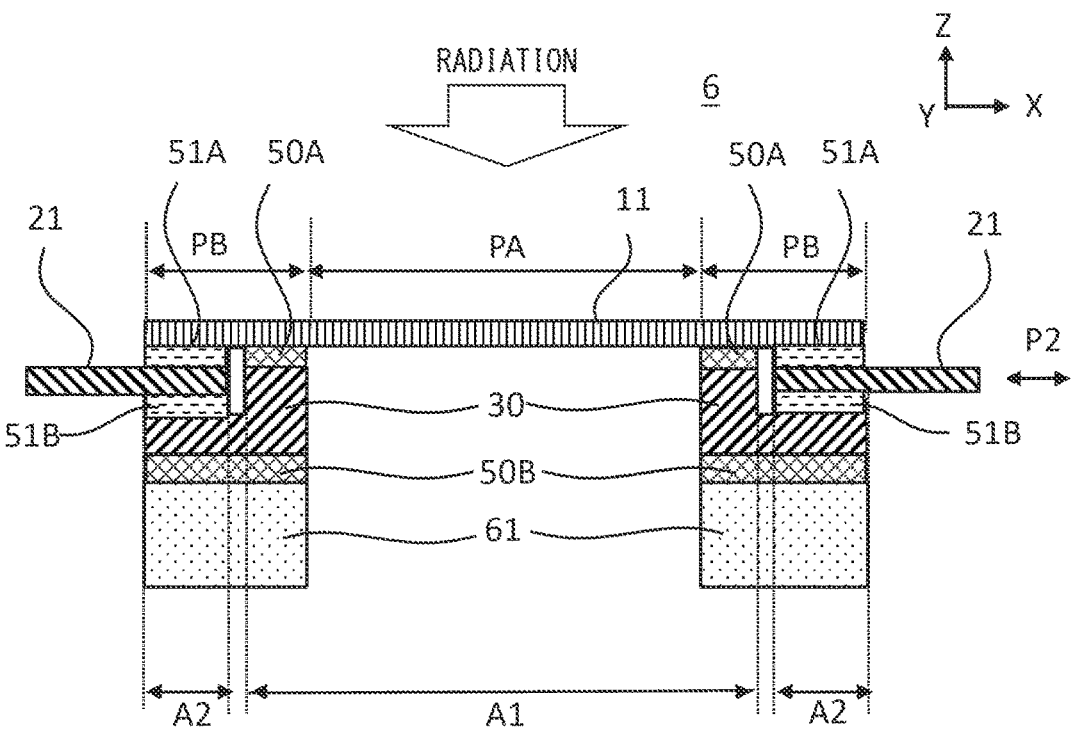
FIG. 17A is a schematic section view of a radiation detector according to a sixth embodiment.
Figure 17B:
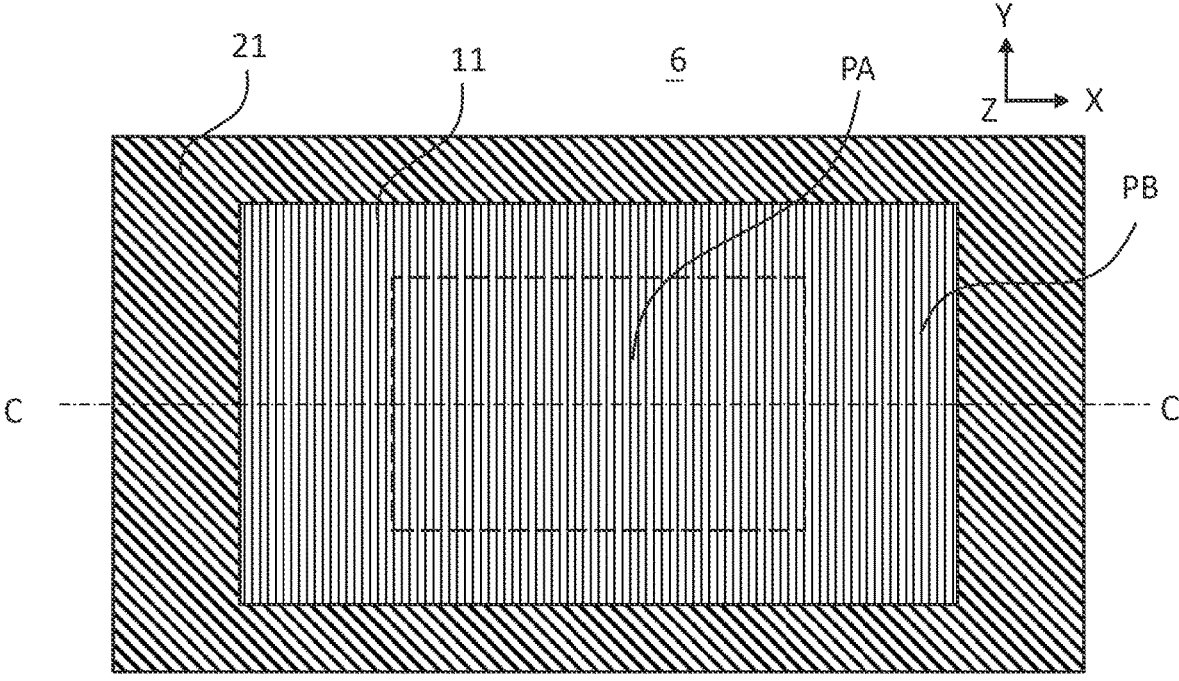
FIG. 17B is a schematic plan view of the radiation detector according to the sixth embodiment.

A radiation detector according to a sixth embodiment will be described. For elements common to the first and second embodiments, description may be simplified or omitted.
Configuration of Radiation Detector FIG. 17B is a plan view of a radiation detector 6 according to the present embodiment as viewed in a radiation incident direction, and FIG. 17A illustrates a cross-section taken along a line C-C in FIG. 17B. As illustrated in FIG. 17A, the heat conducting member 30 serving as a first member and the circuit board 21 serving as a second member are provided as viewed along the plane P2 parallel to the main surface of the semiconductor layer 11. The radiation detector 6 is the same as the radiation detector 1 of the first embodiment in that the radiation detector 6 includes the semiconductor layer 11, the circuit board 21, the heat conducting member 30, and the cooling device 61, but is different from the radiation detector 1 in that the heat conducting member 30 and the cooling device 61 are not disposed on the back surface side of the detection region PA serving as a light receiving portion. In the present embodiment, there is a space between the adhesive layer 51A and the first buffer member 50A and between the heat conducting member 30 and the circuit board 21. According to the present embodiment, since a space where no member is disposed is provided on the back surface side of the detection region PA, radiation having passed through the semiconductor layer 11 is not reflected in the vicinity of the back surface of the detection region PA or does not cause discharge of secondary particles. Therefore, generation of a noise in the semiconductor layer 11 as a result of an influence from the back surface side can be suppressed. Description of each member is the same as in the fifth embodiment, and will be therefore omitted.
Attachment of Radiation Detector A procedure of attaching the radiation detector according to the present embodiment to the radiation detection apparatus will be described with reference to FIGS. 18A to 18C. In addition, as a fifth comparative embodiment, an example of coupling the semiconductor layer 11 and the heat conducting member 30 by using only an adhesive layer without using a first buffer member in the region A1 will be described with reference to FIGS. 19A to 19C. To be noted, for the sake of convenience of illustration, only the right end side in FIG. 17A is illustrated in these section views.

Figure 19A:
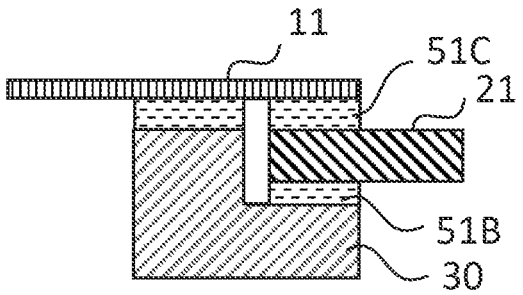
FIG. 19A is a diagram illustrating a unit formation step of a radiation detector according to a fifth comparative embodiment.
Figure 19A:
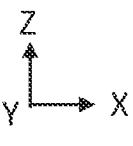

First, the fifth comparative embodiment will be described. First, as illustrated in FIG. 19A, a unit is formed by coupling the semiconductor layer 11, the circuit board 21, and the heat conducting member 30 by the adhesive layer 51C and the adhesive layer 51B. At this time, each member is positioned by using a jig or the like such that an excessive force is not applied to the semiconductor layer 11, and the radiation detection unit is formed by fixing each member by using an adhesive.

Figure 19B:
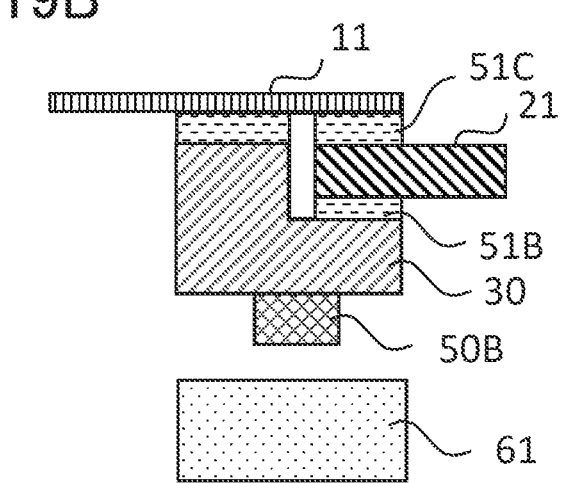
FIG. 19B is an attachment preparation step of the radiation detector according to the fifth comparative embodiment.
Figure 19B:
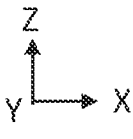

Next, as illustrated in FIG. 19B, the second buffer member 50B (for example, an appropriate amount of grease) is applied on the lower surface of the heat conducting member 30, and alignment in the X and Y directions is performed while the heat conducting member 30 and the cooling device 61 are separated in the Z direction. To be noted, the second buffer member 50B may be applied on the upper surface of the cooling device 61 instead of the lower surface of the heat conducting member 30, or may be applied on both the lower surface of the heat conducting member 30 and the upper surface of the cooling device 61 in some cases.

Figure 19C:
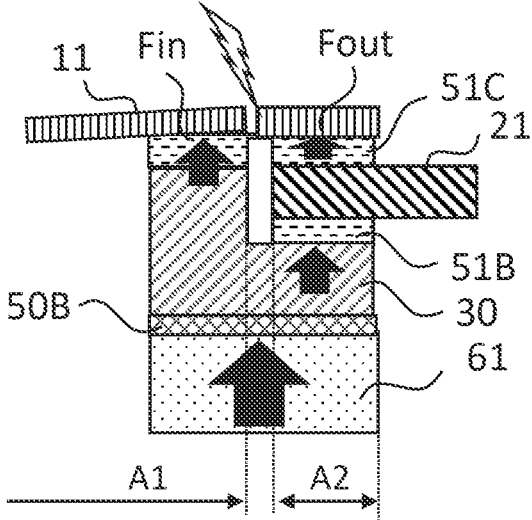
FIG. 19C is a diagram schematically illustrating a force acting when attaching the radiation detector according to the fifth comparative embodiment.
Figure 19C:
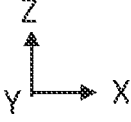

Next, as illustrated in FIG. 19C, the cooling device 61 and the heat conducting member 30 are made closer to each other in the Z direction, and are coupled via the second buffer member 50B. In FIG. 19C, force acting on each portion in this case is schematically indicated by an arrow. Since the heat conducting member 30 has high rigidity, the heat conducting member 30 transmits force of the same magnitude in the Z direction in both the region A1 and the region A2. However, in the region A2, since the circuit board 21 having a lower elastic modulus than the heat conducting member 30 is sandwiched between the adhesive layer 51C and the adhesive layer 51B, and the force in the Z direction is transmitted to the semiconductor layer 11 via these layers, the force Fout applied to the semiconductor layer 11 is smaller than the force of the heat conducting member 30 pressing the adhesive layer 51B. In contrast, in the region A1, the heat conducting member 30 directly presses the adhesive layer 51C in the Z direction, and since the circuit board 21 having a low elastic modulus is not present therebetween, the force Fin acting on the semiconductor layer 11 in the Z direction is remarkably larger than the force Fout. Therefore, excessive stress (resultant force of shearing force, tensile force, and compressive force) locally acts on the semiconductor layer 11 in the vicinity of the boundary between the region A1 and the region A2, and thus the semiconductor layer 11 is easily damaged.

Figure 18A:
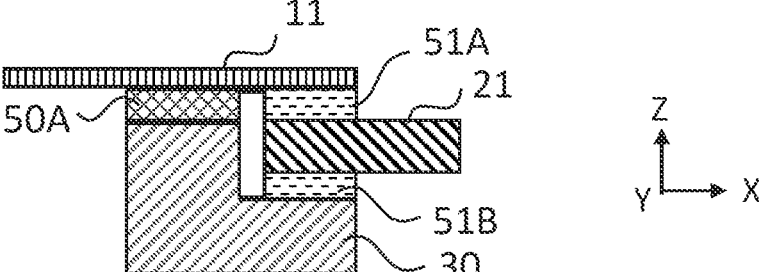
FIG. 18A is a diagram illustrating a unit formation step of the radiation detector according to the sixth embodiment.

Next, the present embodiment will be described. In the present embodiment, as illustrated in FIG. 18A, a unit is formed by coupling the semiconductor layer 11, the circuit board 21, and the heat conducting member 30 by the adhesive layer 51A, the adhesive layer 51B, and the first buffer member 50A. At this time, each member is positioned by using a jig or the like such that an excessive force is not applied to the semiconductor layer 11, and each member is fixed by using the adhesive and first buffer member.

Figure 18B:
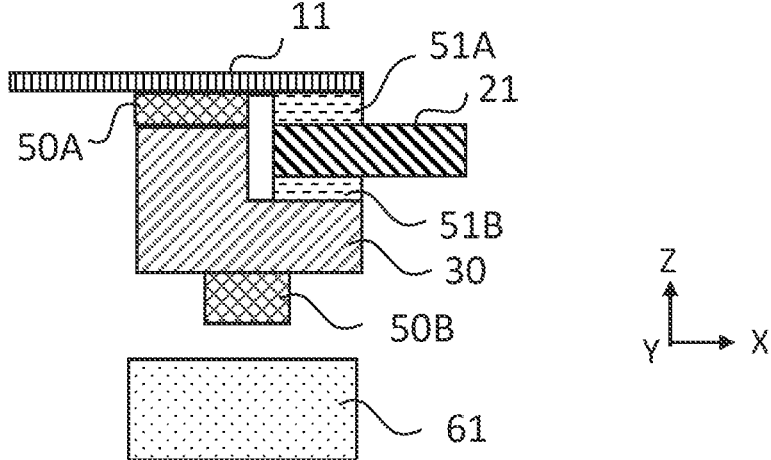
FIG. 18B is an attachment preparation step of the radiation detector according to the sixth embodiment.

Next, as illustrated in FIG. 18B, the second buffer member 50B (for example, an appropriate amount of grease) is applied on the lower surface of the heat conducting member 30, and alignment in the X and Y directions is performed while the heat conducting member 30 and the cooling device 61 are separated in the Z direction. To be noted, the second buffer member 50B may be applied on the upper surface of the cooling device 61 instead of the lower surface of the heat conducting member 30, or may be applied on both the lower surface of the heat conducting member 30 and the upper surface of the cooling device 61 in some cases. To be noted, by coupling via a second buffer member 50B, the workability can be improved not only when attaching a radiation detection unit including a semiconductor layer to the cooling device 61 but also when separating an old radiation detection unit from the cooling device 61 to replace the radiation detector.

Figure 18C:
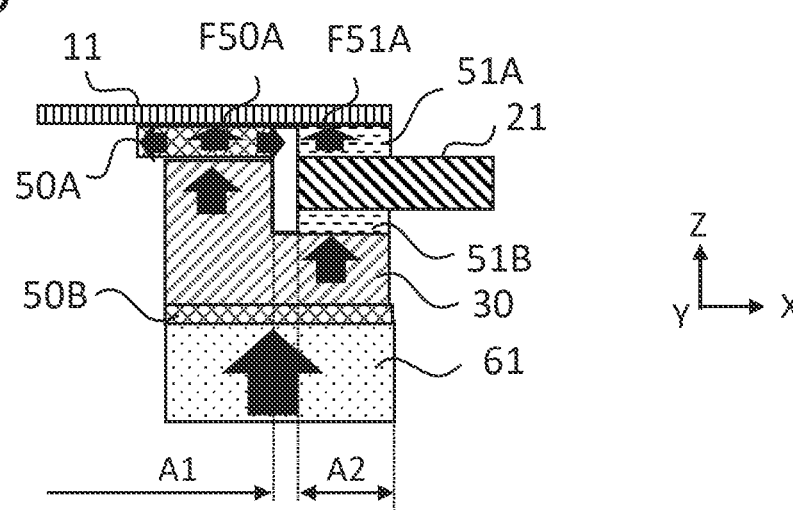
FIG. 18C is a diagram schematically illustrating a force acting when attaching the radiation detector according to the sixth embodiment.

Next, as illustrated in FIG. 18C, the cooling device 61 and the heat conducting member 30 are made closer to each other in the Z direction, and are coupled via the second buffer member 50B. In FIG. 18C, force acting on each portion in this case is schematically indicated by an arrow. Since the heat conducting member 30 has high rigidity, the heat conducting member 30 transmits force of the same magnitude in the Z direction in both the region A1 and the region A2. However, in the region A2, since the circuit board 21 having a lower elastic modulus than the heat conducting member 30 is sandwiched between the adhesive layer 51A and the adhesive layer 51B, and the force in the Z direction is transmitted to the semiconductor layer 11 via these layers, the force F51A applied to the semiconductor layer 11 is smaller than the force of the heat conducting member 30 pressing the adhesive layer 51B. In contrast, in the region A1, the heat conducting member 30 presses the first buffer member 50A (for example, grease) in the Z direction, and since the first buffer member 50A is formed from an easily deformable material, the first buffer member 50A deforms to spread to an adjacent space in the X-Y plane. In addition, since there is a space between the adhesive layer 51A and the first buffer member 50A, the space adjacent in the X-Y plane is larger than in the second embodiment. Therefore, part of the pressing force from the heat conducting member 30 in the Z direction is used for the deformation of the first buffer member 50A in the X-Y plane and in the space between the adhesive layer 51A and the first buffer member 50A, and therefore the force F50A applied from the first buffer member 50A to the semiconductor layer 11 is smaller than the force of the heat conducting member 30 pressing the first buffer member 50A in the Z direction. As a result, the difference in the force in the Z direction acting on the semiconductor layer 11 between the regions A1 and A2 is reduced, and damaging of the semiconductor layer 11 in the vicinity of the boundary between the regions A1 and A2 can be suppressed.

As described above, according to the present embodiment, damaging of the semiconductor layer of the radiation detector can be suppressed when attaching the radiation detector for manufacturing the radiation detection apparatus or when replacing a radiation detector whose characteristics have deteriorated with a new radiation detector.

Seventh Embodiment

Figures 20A, 20B:
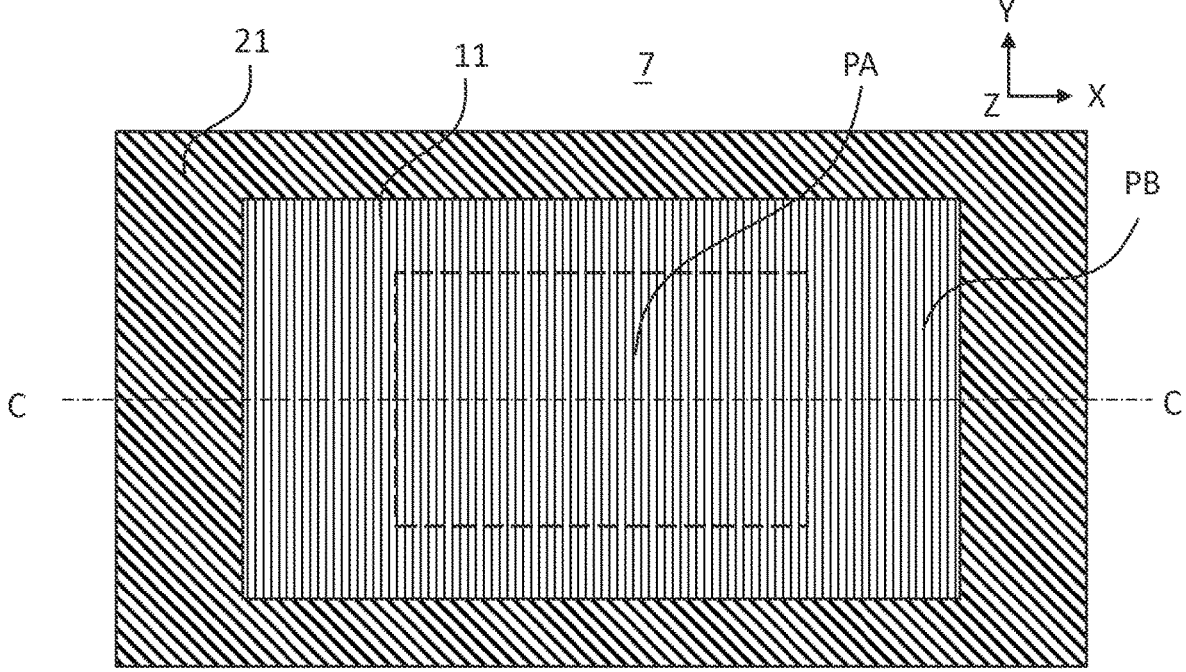
FIG. 20A is a schematic section view of a radiation detector according to a seventh embodiment.
FIG. 20B is a schematic plan view of the radiation detector according to the seventh embodiment.

A radiation detector according to a seventh embodiment will be described. For elements common to the first to third embodiments, description may be simplified or omitted.
Configuration of Radiation Detector FIG. 20B is a plan view of a radiation detector 7 according to the present embodiment as viewed in a radiation incident direction, and FIG. 20A illustrates a cross-section taken along a line C-C in FIG. 20B. The radiation detector 7 includes the semiconductor layer 11, the circuit board 21, the heat conducting member 30A serving as a first heat conducting member, the heat conducting member 30B serving as a second heat conducting member, and the cooling device 61. As illustrated in FIG. 20A, the heat conducting member 30A serving as a first member and the circuit board 21 serving as a second member are provided as viewed along the plane P3 parallel to the main surface of the semiconductor layer 11. Description of the semiconductor layer 11, the circuit board 21, and the cooling device 61 is substantially the same as in the first embodiment, and will be therefore omitted. In addition, description of the materials and physical properties of the adhesive layers and buffer members used in the present embodiment is common to the first embodiment, and will be therefore omitted.

Whereas the radiation detector 1 of the first embodiment includes the single heat conducting member 30, the radiation detector 7 of the present embodiment is different in that the radiation detector 7 includes two of the heat conducting member 30A serving as a first heat conducting member and the heat conducting member 30B serving as a second heat conducting member. In the present embodiment, in the region A2, the semiconductor layer 11 and the heat conducting member 30A are stuck together instead of coupling the semiconductor layer 11 and the circuit board 21 via an adhesive layer, and therefore heat can be efficiently dissipated to the heat conducting member 30A from a peripheral region of the semiconductor layer 11.

Similarly to the description of the first embodiment, when viewed in the Z direction that is perpendicular to the main surface of the semiconductor layer 11, a region where the circuit board 21 and a gap between the circuit board 21 and the heat conducting member 30A are not present between the cooling device 61 and the semiconductor layer 11 will be referred to as a region A1, and a region where the circuit board 21 is present between the cooling device 61 and the semiconductor layer 11 will be referred to as a region A2.

In the case where a main surface on which the radiation is incident is referred to as a front surface and a main surface opposite thereto is referred to as a back surface in the semiconductor layer 11, the back surface of the detection region PA opposes the heat conducting member 30A with a space therebetween. In addition, in a part of the peripheral region PB belonging to the region A1, the semiconductor layer 11, the adhesive layer 51D, the heat conducting member 30A, the first buffer member 50C, the heat conducting member 30B, the second buffer member 50D, and the cooling device 61 are laminated in this order. In addition, in a part of the peripheral region PB belonging to the region A2, the semiconductor layer 11, the adhesive layer 51D, the heat conducting member 30A, the adhesive layer 51E, the circuit board 21, the adhesive layer 51F, the heat conducting member 30B, the second buffer member 50D, and the cooling device 61 are laminated in this order. In the present embodiment, there is a gap between the adhesive layer 51E and the heat conducting member 30A, and there is a gap between the adhesive layer 51F and the first buffer member 50C.

Attachment of Radiation Detector

Figure 21A:
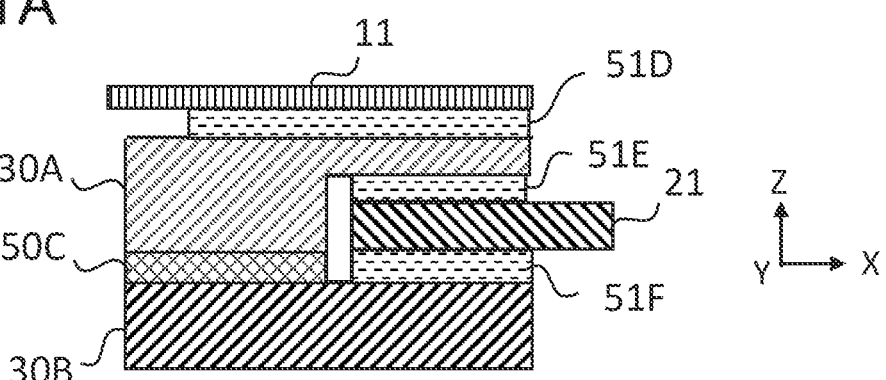
FIG. 21A is a diagram illustrating a unit formation step of the radiation detector according to the seventh embodiment.

A procedure of attaching the radiation detector according to the present embodiment to the radiation detection apparatus will be described with reference to FIGS. 21A to 21C. In addition, as a sixth comparative embodiment, an example of coupling the heat conducting member 30A and the heat conducting member 30B by using only the adhesive layer 51F without using the first buffer member 50C in the region A1 will be described with reference to FIGS. 22A to 22C. To be noted, for the sake of convenience of illustration, only the right end side in FIG. 20A is illustrated in these section views.

Figure 22A:
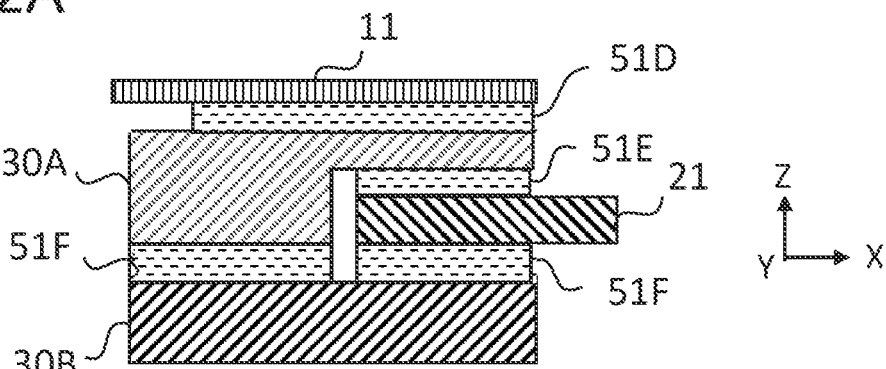
FIG. 22A is a diagram illustrating a unit formation step of a radiation detector according to a sixth comparative embodiment.

First, the sixth comparative embodiment will be described. First, as illustrated in FIG. 22A, a unit is formed by coupling the semiconductor layer 11, the circuit board 21, the heat conducting member 30A, and the heat conducting member 30B by the adhesive layer 51D, the adhesive layer 51E, and the adhesive layer 51F. At this time, each member is positioned by using a jig or the like such that an excessive force is not applied to the semiconductor layer 11, and the radiation detection unit is formed by fixing each member by using an adhesive.

Figure 22B:
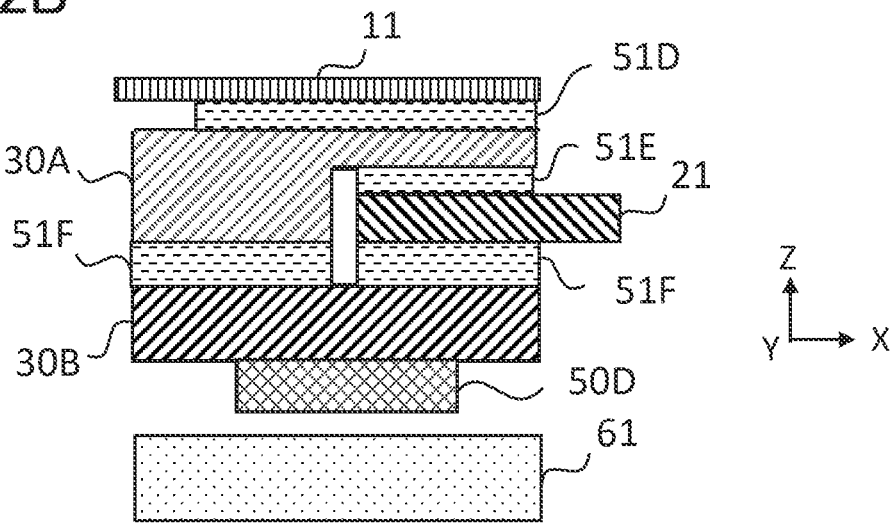
FIG. 22B is an attachment preparation step of the radiation detector according to the sixth comparative embodiment.

Next, as illustrated in FIG. 22B, the second buffer member 50D (for example, an appropriate amount of grease) is applied on the lower surface of the heat conducting member 30B, and alignment in the X and Y directions is performed while the heat conducting member 30B and the cooling device 61 are separated in the Z direction. To be noted, the second buffer member 50D may be applied on the upper surface of the cooling device 61 instead of the lower surface of the heat conducting member 30B, or may be applied on both the lower surface of the heat conducting member 30B and the upper surface of the cooling device 61 in some cases.

Figure 22C:
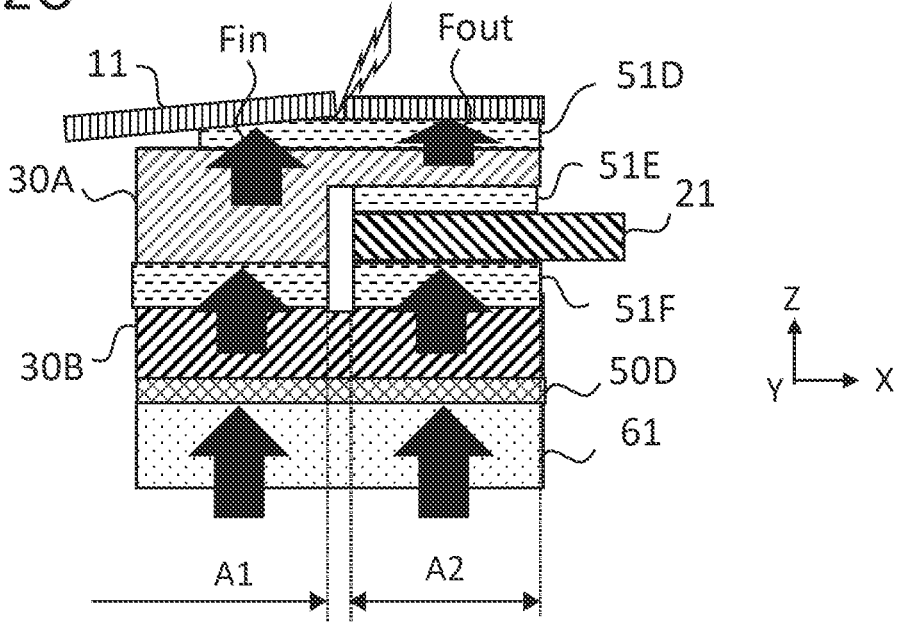
FIG. 22C is a diagram schematically illustrating a force acting when attaching the radiation detector according to the sixth comparative embodiment.

Next, as illustrated in FIG. 22C, the cooling device 61 and the heat conducting member 30B are made closer to each other in the Z direction, and are coupled via the second buffer member 50D. In FIG. 22C, force acting on each portion in this case is schematically indicated by an arrow. Since the heat conducting member 30B has high rigidity, the heat conducting member 30B transmits force of the same magnitude in the Z direction in both the region A1 and the region A2.

In the region A1, the force in the Z direction is transmitted from the heat conducting member 30B to the heat conducting member 30A via only the adhesive layer 51F. However, in the region A2, the circuit board 21 having a lower elastic modulus than the heat conducting member 30A is sandwiched between the adhesive layer 51F and the adhesive layer 51E, and the force in the Z direction is transmitted from the heat conducting member 30B to the heat conducting member 30A via these layers. Therefore, regarding the force in the Z direction applied to the semiconductor layer 11 from the heat conducting member 30A via the adhesive layer 51D, the force Fin in the region A1 is remarkably larger than the force Fout in the region A2. Therefore, excessive stress (resultant force of shearing force, tensile force, and compressive force) locally acts on the semiconductor layer 11 in the vicinity of the boundary between the region A1 and the region A2, and thus the semiconductor layer 11 is easily damaged.

Next, the present embodiment will be described. In the present embodiment, as illustrated in FIG. 21A, first, a unit is formed by coupling the semiconductor layer 11, the circuit board 21, the heat conducting member 30A, and the heat conducting member 30B by the adhesive layer 51D, the adhesive layer 51E, the adhesive layer 51F, and the first buffer member 50C. At this time, each member is positioned by using a jig or the like such that an excessive force is not applied to the semiconductor layer 11, and each member is fixed by using the adhesive and buffer member.

Figure 21B:
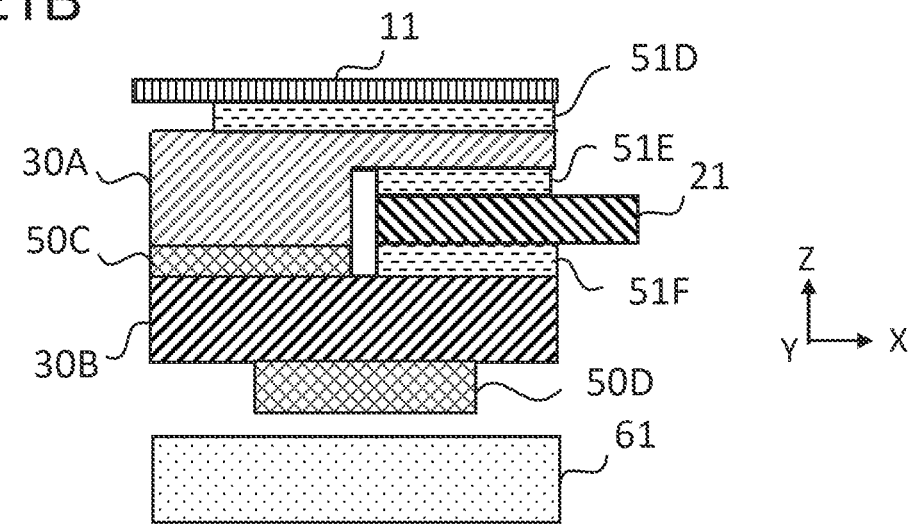
FIG. 21B is an attachment preparation step of the radiation detector according to the seventh embodiment.

Next, as illustrated in FIG. 21B, the second buffer member 50D (for example, an appropriate amount of grease) is applied on the lower surface of the heat conducting member 30B, and alignment in the X and Y directions is performed while the heat conducting member 30B and the cooling device 61 are separated in the Z direction. To be noted, the second buffer member 50D may be applied on the upper surface of the cooling device 61 instead of the lower surface of the heat conducting member 30B, or may be applied on both the lower surface of the heat conducting member 30B and the upper surface of the cooling device 61 in some cases. To be noted, by coupling via the second buffer member 50D, the workability can be improved not only when attaching a radiation detection unit including a semiconductor layer to the cooling device 61 but also when separating an old radiation detection unit from the cooling device 61 to replace the radiation detector.

Figure 21C:
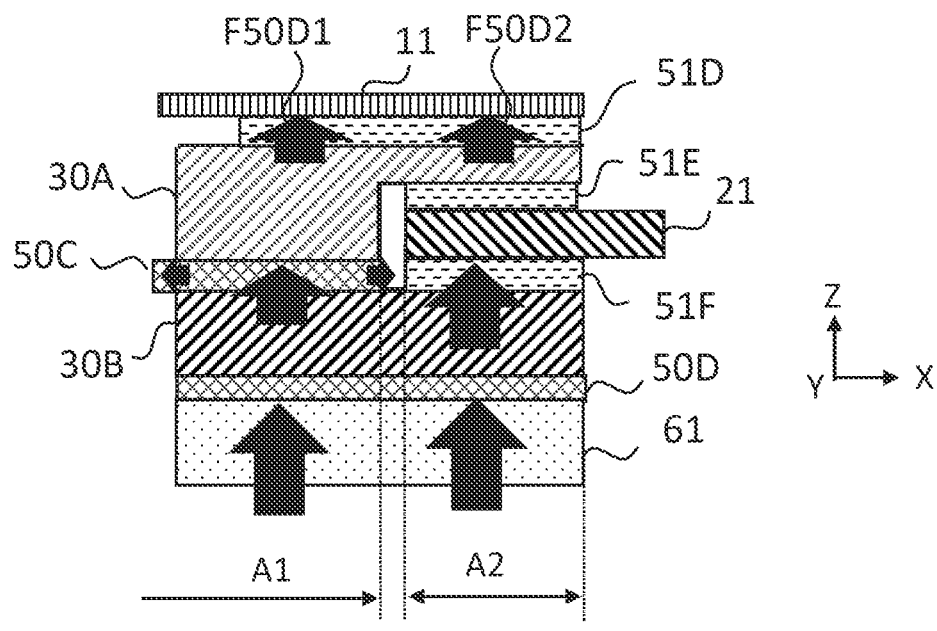
FIG. 21C is a diagram schematically illustrating a force acting when attaching the radiation detector according to the seventh embodiment.

Next, as illustrated in FIG. 21C, the cooling device 61 and the heat conducting member 30B are made closer to each other in the Z direction, and are coupled via the second buffer member 50D. In FIG. 21C, force acting on each portion in this case is schematically indicated by an arrow. Since the heat conducting member 30B has high rigidity, the heat conducting member 30B transmits force of the same magnitude in the Z direction in both the region A1 and the region A2.

In the region A1, force is transmitted from the heat conducting member 30B to the heat conducting member 30A via the first buffer member 50C, and since the first buffer member 50C is formed from an easily deformable material, the first buffer member 50C deforms to spread to an adjacent space in the X-Y plane. In addition, since there is a space between the adhesive layer 51F and the first buffer member 50C, the space adjacent to the first buffer member 50C in the X-Y plane is larger than in the third embodiment. Therefore, part of the pressing force from the heat conducting member 30B in the Z direction is used for the deformation of the first buffer member 50C in the X-Y plane and in the space between the adhesive layer 51F and the first buffer member 50C, and therefore the force applied from the first buffer member 50C to the heat conducting member 30A is smaller than the force of the heat conducting member 30B pressing the first buffer member 50C in the Z direction.

In the region A2, the circuit board 21 having a lower elastic modulus than the heat conducting member 30A is sandwiched between the adhesive layer 51F and the adhesive layer 51E, and the force in the Z direction is transmitted from the heat conducting member 30B to the heat conducting member 30A via these layers. Therefore, the force applied from the adhesive layer 51E to the heat conducting member 30A is smaller than the force of the heat conducting member 30B pressing the adhesive layer 51F in the Z direction.

As a result, regarding the force in the Z direction acting on the semiconductor layer 11, the difference between the force F50D1 in the region A1 and the force F50D2 in the region A2 is reduced, and damaging of the semiconductor layer 11 in the vicinity of the boundary between the regions A1 and A2 can be suppressed.

As described above, according to the present embodiment, damaging of the semiconductor layer of the radiation detector can be suppressed when attaching the radiation detector for manufacturing the radiation detection apparatus or when replacing a radiation detector whose characteristics have deteriorated with a new radiation detector.

Eighth Embodiment

Figure 23A:
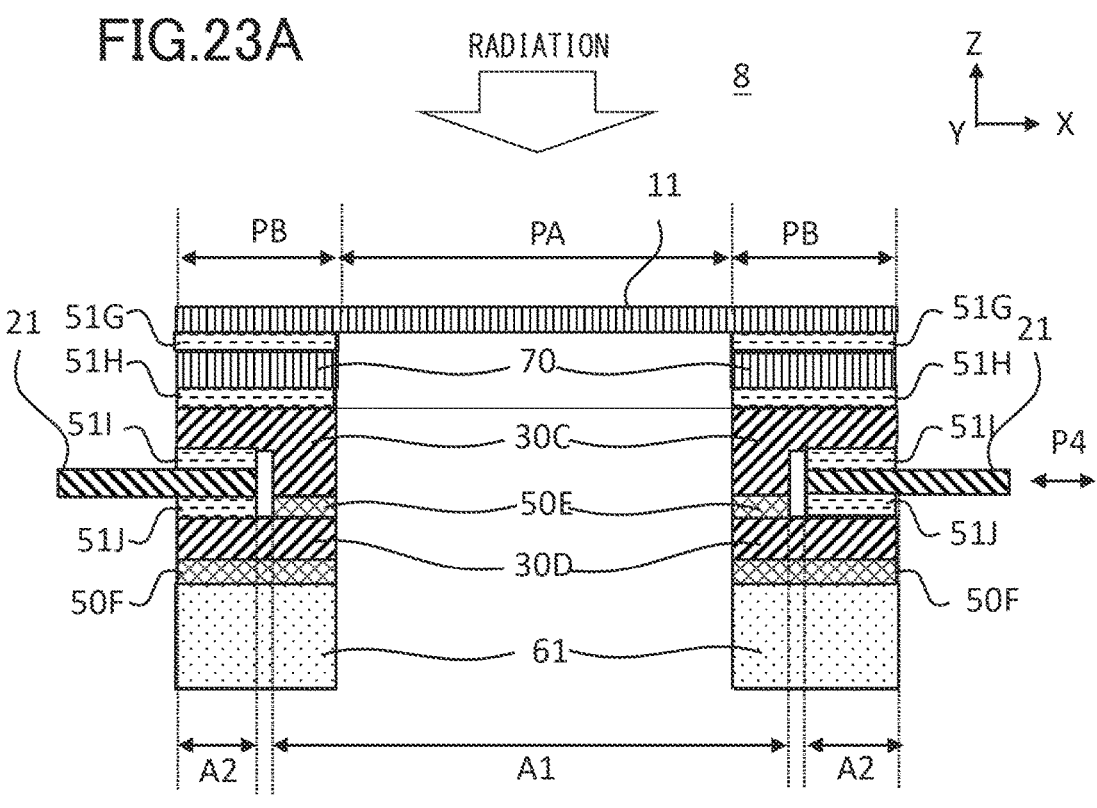
FIG. 23A is a schematic section view of a radiation detector according to an eighth embodiment.
Figure 23B:
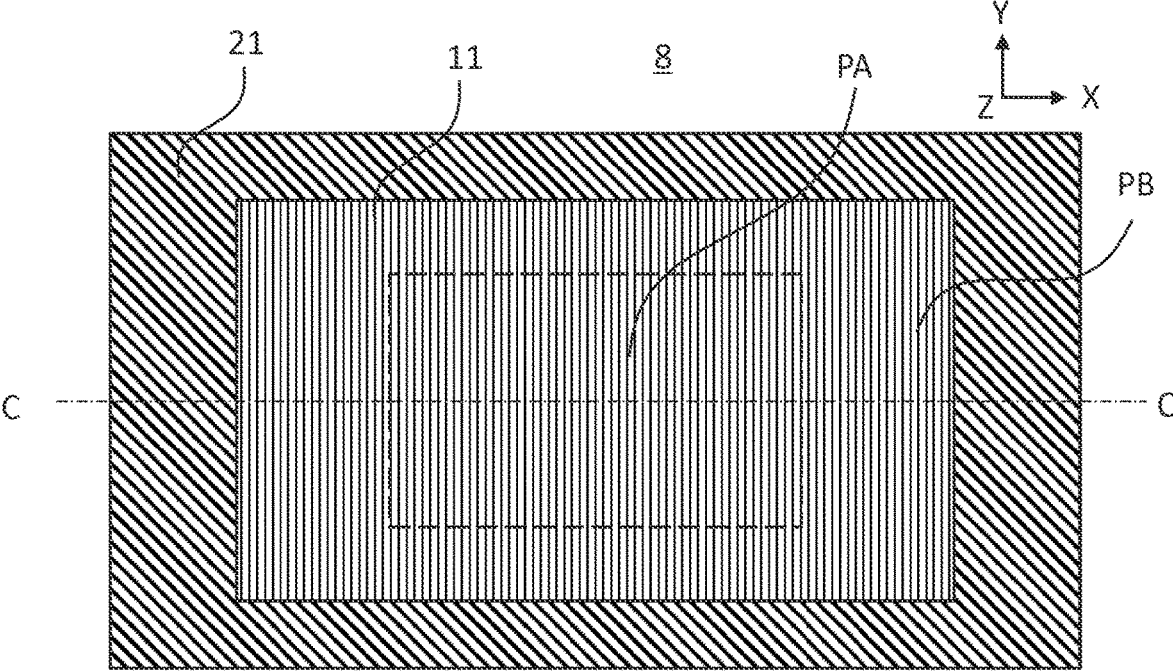
FIG. 23B is a schematic plan view of the radiation detector according to the eighth embodiment.

A radiation detector according to an eighth embodiment will be described. For elements common to the first to fourth embodiments, description may be simplified or omitted.
Configuration of Radiation Detector
FIG. 23B is a plan view of a radiation detector 8 according to the present embodiment as viewed in a radiation incident direction, and FIG. 23A illustrates a cross-section taken along a line C-C in FIG. 23B. As illustrated in FIG. 23A, a heat conducting member 30C serving as a first member and the circuit board 21 serving as a second member are provided as viewed along the plane P4 parallel to the main surface of the semiconductor layer 11. The radiation detector 8 includes the semiconductor layer 11, the support member 70, the heat conducting member 30C serving as a first heat conducting member, the circuit board 21, the heat conducting member 30D serving as a second heat conducting member, and the cooling device 61. The present invention is the same as the second embodiment in that no heat conducting member or cooling device is disposed on the back surface side of the detection region PA serving as a light receiving portion. That is, also in the present embodiment, since a space where no member is disposed is provided on the back surface side of the detection region PA, radiation having passed through the semiconductor layer 11 is not reflected in the vicinity of the back surface of the detection region PA or does not cause discharge of secondary particles. Therefore, generation of a noise in the semiconductor layer 11 as a result of an influence from the back surface side can be suppressed.

Description of the semiconductor layer 11, the circuit board 21, and the cooling device 61 is substantially the same as in the first embodiment, and will be therefore omitted. In addition, description of the materials and physical properties of the adhesive layers and buffer members used in the present embodiment is common to the first embodiment, and will be therefore omitted. In addition, description of the heat conducting member 30C and the heat conducting member 30D follows the description of the heat conducting member 30A and the heat conducting member 30B in the third embodiment, and is therefore omitted.

The radiation detector 8 of the present embodiment includes the support member 70 between the semiconductor layer 11 and the heat conducting member 30C serving as a first heat conducting member. The support member 70 can be formed in, for example, a frame shape or a tube shape surrounding the detection region PA in plan view as viewed in a direction perpendicular to the semiconductor layer. As the material constituting the support member 70, a material having a line expansion coefficient equal to that of the semiconductor layer 11 or between those of the semiconductor layer 11 and the heat conducting member 30C can be used. In the case where the semiconductor layer 11 and an underlayer member thereof have different thermal expansion coefficients, shape difference occurs when cooling the semiconductor layer 11 by using the cooling device 61, and the semiconductor layer 11 having low mechanical strength can be damaged due to the deformation. In the present embodiment, the support member 70 formed from a material having a line expansion coefficient equal to that of the semiconductor layer 11 or between those of the semiconductor layer 11 and the heat conducting member 30C is interposed between the semiconductor layer 11 and the heat conducting member 30C. As a result of this, the shape difference between the semiconductor layer 11 and the underlayer member is relieved when cooling the semiconductor layer 11, and thus the risk of damaging of the semiconductor layer 11 can be reduced. For example, in the case where the material of the semiconductor layer 11 is silicon and the material of the heat conducting member 30C is CuW, silicon or aluminum nitride is preferably used as the material of the support member 70. That is, the material is selected such that the thermal expansion coefficient of the support member 70 is equal to or higher than the thermal expansion coefficient of the semiconductor layer 11 and lower than the thermal expansion coefficient of the heat conducting member 30C. The support member 70 is preferably thicker than the semiconductor layer 11 so as to have higher mechanical strength than the semiconductor layer 11.
Attachment of Radiation Detector
A procedure of attaching the radiation detector according to the present embodiment to the radiation detection apparatus will be described with reference to FIGS. 24A to 24C. To be noted, for the sake of convenience of illustration, only the right end side in FIG. 23A is illustrated in these section views.

Figure 24A:
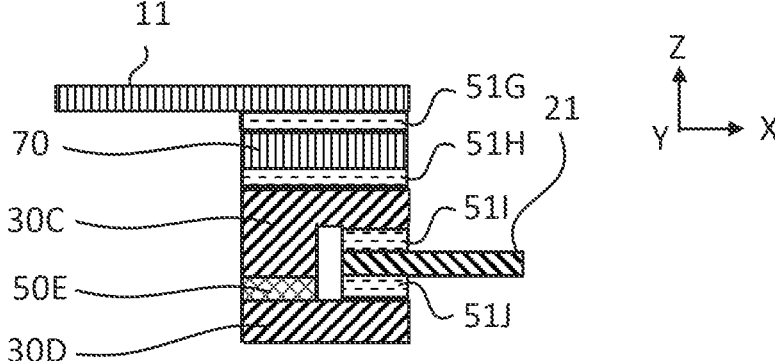
FIG. 24A is a diagram illustrating a unit formation step of the radiation detector according to the eighth embodiment.

In the present embodiment, as illustrated in FIG. 24A, first, a unit is formed by coupling the semiconductor layer 11, the support member 70, the heat conducting member 30C, the circuit board 21, and the heat conducting member 30D by the adhesive layer 51G, the adhesive layer 51H, the adhesive layer 51I, the adhesive layer 51J, and the first buffer member 50E. At this time, each member is positioned by using a jig or the like such that an excessive force is not applied to the semiconductor layer 11, and each member is fixed by using the adhesive and buffer member.

Figure 24B:
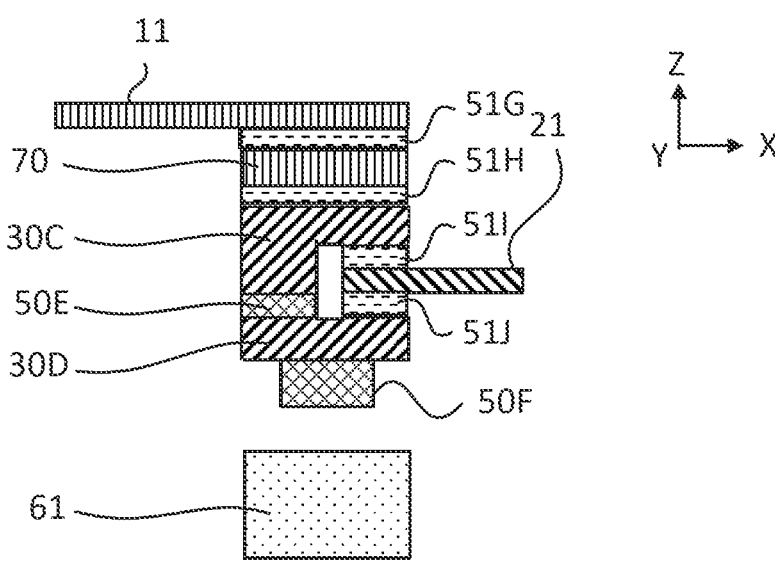
FIG. 24B is an attachment preparation step of the radiation detector according to the eighth embodiment.

Next, as illustrated in FIG. 24B, a second buffer member 50F (for example, an appropriate amount of grease) is applied on the lower surface of the heat conducting member 30D, and alignment in the X and Y directions is performed while the heat conducting member 30D and the cooling device 61 are separated in the Z direction. To be noted, the second buffer member 50F may be applied on the upper surface of the cooling device 61 instead of the lower surface of the heat conducting member 30D, or may be applied on both the lower surface of the heat conducting member 30D and the upper surface of the cooling device 61 in some cases. To be noted, by coupling via the second buffer member 50F, the workability can be improved not only when attaching a radiation detection unit including a semiconductor layer to the cooling device 61 but also when separating an old radiation detection unit from the cooling device 61 to replace the radiation detector.

Figure 24C:
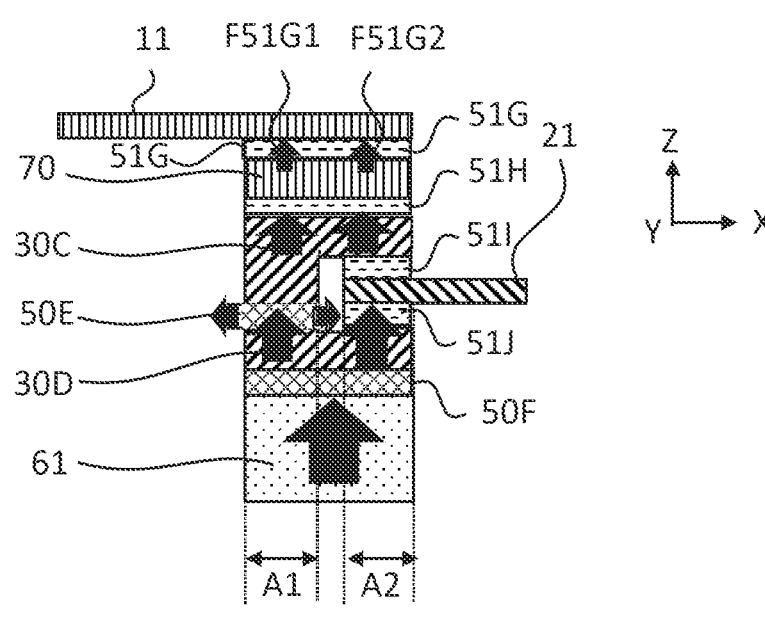
FIG. 24C is a diagram schematically illustrating a force acting when attaching the radiation detector according to the eighth embodiment.

Next, as illustrated in FIG. 24C, the cooling device 61 and the heat conducting member 30D are made closer to each other in the Z direction, and are coupled via the second buffer member 50F. In FIG. 24C, force acting on each portion in this case is schematically indicated by an arrow. Since the heat conducting member 30D has high rigidity, the heat conducting member 30D transmits force of the same magnitude in the Z direction in both the region A1 and the region A2.

In the region A1, force is transmitted from the heat conducting member 30D to the heat conducting member 30C via the first buffer member 50E, and since the first buffer member 50E is formed from an easily deformable material, the first buffer member 50E deforms to spread to an adjacent space in the X-Y plane. In addition, since there is a space between the adhesive layer 51J and the first buffer member 50E, the space adjacent in the X-Y plane is larger than in the fourth embodiment. Therefore, part of the pressing force from the heat conducting member 30D in the Z direction is used for the deformation of the first buffer member 50E in the X-Y plane and in the space between the adhesive layer 51J and the first buffer member 50E, and therefore the force applied from the first buffer member 50E to the heat conducting member 30C is smaller than the force of the heat conducting member 30D pressing the first buffer member 50E in the Z direction.

In the region A2, the circuit board 21 having a lower elastic modulus than the heat conducting member 30C is sandwiched between the adhesive layer 51J and the adhesive layer 51I, and the force in the Z direction is transmitted from the heat conducting member 30D to the heat conducting member 30C via these layers. Therefore, the force applied from the adhesive layer 51I to the heat conducting member 30C is smaller than the force of the heat conducting member 30D pressing the adhesive layer 51J in the Z direction.

As a result, regarding the force in the Z direction acting on the semiconductor layer 11 via the support member 70 and the adhesive layer 51G, the difference between the force F51G1 in the region A1 and the force F51G2 in the region A2 is reduced, and damaging of the semiconductor layer 11 in the vicinity of the boundary between the regions A1 and A2 can be suppressed.

As described above, according to the present embodiment, damaging of the semiconductor layer of the radiation detector can be suppressed when attaching the radiation detector for manufacturing the radiation detection apparatus or when replacing a radiation detector whose characteristics have deteriorated with a new radiation detector.

Ninth Embodiment

Figure 12:
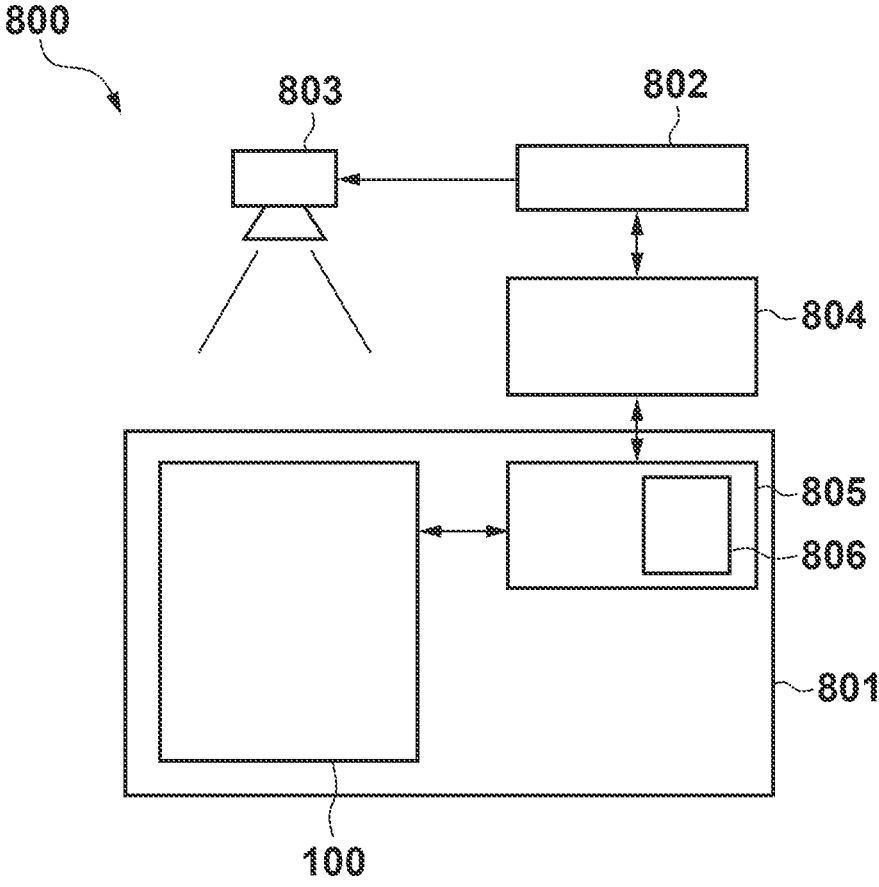
FIG. 12 is a schematic diagram for describing a radiation imaging system according to a ninth embodiment.

A radiation imaging apparatus 801 incorporating the radiation detector of any one of the first to eighth embodiments described above, and a radiation imaging system 800 including the radiation imaging apparatus 801 will be described with reference to FIG. 12.

The radiation imaging system 800 is configured to electrically capture an optical image formed by radiation, and thus obtain an electrical radiation image, that is, radiation image data. The radiation imaging system 800 includes, for example, the radiation imaging apparatus 801, an irradiation controller 802, a radiation source 803, and a computer 804. The radiation imaging system 800 is capable of displaying the obtained radiation image on an unillustrated display apparatus, and transmitting radiation image data to the outside via an unillustrated communication apparatus. The radiation imaging system 800 can be preferably used in the fields of, for example, medical image diagnosis and non-destructive inspection.

The radiation source 803 for emitting radiation starts the emission of the radiation in accordance with an irradiation command from the irradiation controller 802. The radiation emitted from the radiation source 803 irradiates the radiation imaging apparatus 801 through an unillustrated inspection target. The radiation source 803 stops the emission of the radiation in accordance with a stop command from the irradiation controller 802.

The radiation imaging apparatus 801 includes a radiation detector 100 according to any one of the first to eighth embodiments described above, a controller 805 for controlling the radiation detector 100, and a signal processor 806 for processing a signal output from the radiation detector.

For example, in the case where the signal output from the radiation detector 100 is an analog signal, the signal processor 806 is capable of performing A/D conversion on the analog signal, and outputting the converted signal to the computer 804 as the radiation image data. In addition, for example, the signal processor 806 may generate a stop signal for stopping the emission of the radiation from the radiation source 803 on the basis of the signal output from the radiation detector 100. The stop signal is supplied to the irradiation controller 802 via the computer 804, and the irradiation controller 802 sends a stop command to the radiation source 803 in response to the stop signal.

The controller 805 can be constituted by, for example, a programmable logic device: PLD such as a field programmable gate array: FPGA, an application specific integrated circuit: ASIC, a general-purpose computer in which a program is installed, or a combination of all or some of these.

In addition, although the signal processor 806 is illustrated as if the signal processor 806 is disposed in the controller 805 or is part of a function of the controller 805, the configuration is not limited to this. The controller 805 and the signal processor 806 may be separately provided. Further, the signal processor 806 may be provided separately from the radiation imaging apparatus 801. For example, the computer 804 may have the function of the signal processor 806. Therefore, the signal processor 806 can be included in the radiation imaging system 800 as a signal processing apparatus that processes the signal output from the radiation imaging apparatus 801.

The computer 804 can control the radiation imaging apparatus 801 and the irradiation controller 802, or perform processing for receiving the radiation image data from the radiation imaging apparatus 801 and displaying the radiation image data as a radiation image. In addition, the computer 804 can function as an input portion for a user to input conditions for imaging of the radiation image.

As an example of the sequence, the irradiation controller 802 includes an irradiation switch, and when the irradiation switch is turned on by the user, the irradiation controller 802 sends an irradiation command to the radiation source 803, and transmits a start notification indicating the start of the emission of the radiation to the computer 804. The computer 804 having received the start notification notifies the controller 805 of the radiation imaging apparatus 801 about the start of the emission of the radiation in response to the start notification. In response to this, the controller 805 causes the radiation detector 100 to generate a signal corresponding to the incident radiation.

In the radiation imaging apparatus and the radiation imaging system including the radiation imaging apparatus of the present embodiment, damaging of the semiconductor layer of the radiation detector can be suppressed when attaching the radiation detector for manufacturing the radiation detection apparatus or when replacing a radiation detector whose characteristics have deteriorated with a new radiation detector. Therefore, a radiation imaging apparatus having excellent reliability and durability and capable of obtaining a radiation image of high image quality can be realized and put into use in various fields such as medical fields and industrial fields.

Tenth Embodiment

Figure 13:
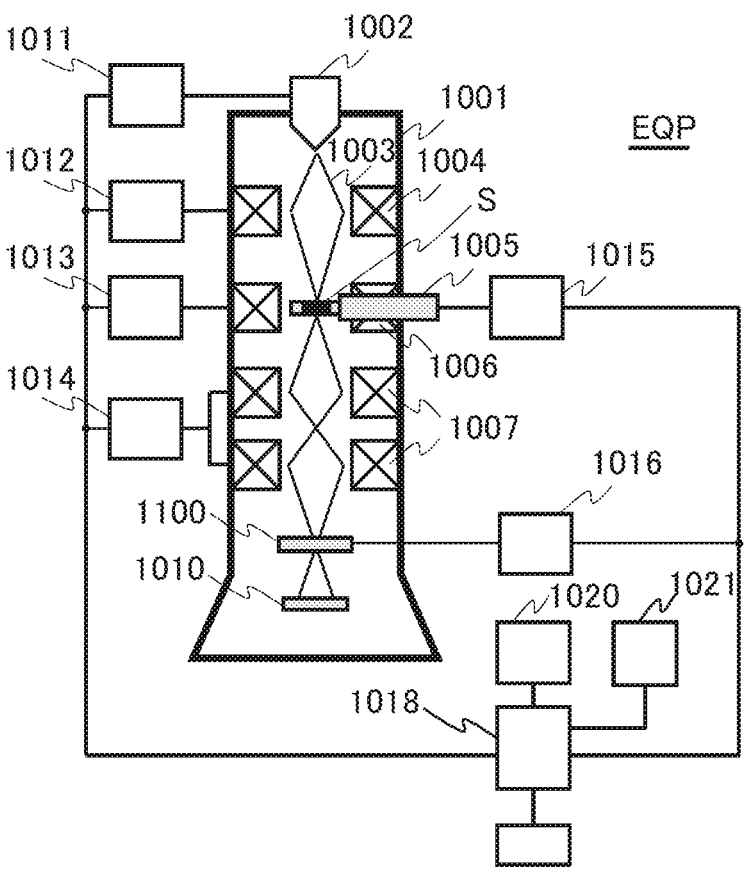
FIG. 13 is a schematic diagram for describing a radiation imaging system according to a tenth embodiment.

As a radiation imaging system including the radiation detector according to any one of the first to eighth embodiments described above, transmission electron microscope (TEM) system will be described with reference to the schematic configuration diagram of FIG. 13. Equipment EQP serving as the transmission electron microscope includes an electron beam source 1002 (electron gun), an irradiation lens 1004, a vacuum chamber 1001 (lens barrel), an objective lens 1006, a magnifying lens system 1007, and a radiation detector 1100.

An electron beam 1003 that is radiation emitted from the electron beam source 1002 (electron gun) serving as a radiation source is converged by the irradiation lens 1004, and is radiated onto a sample S serving as an inspection target held by a sample holder. A space that the electron beam 1003 passes through is defined by the vacuum chamber 1001 (lens barrel) included in the equipment EQP, and this space is maintained at a vacuum.

The electron beam 1003 having passed through the sample S is expanded by the objective lens 1006 and the magnifying lens system 1007, and focused on the light receiving surface of the radiation detector 1100. An electronic optical system for radiating the electron beam onto the sample S will be referred to as an irradiation optical system, and an electronic optical system for focusing the electron beam having passed through the sample S on the light receiving surface of the radiation detector 1100 will be referred to as an imaging optical system.

The electron beam source 1002 is controlled by an electron beam control apparatus 1011. The irradiation lens 1004 is controlled by an irradiation lens control apparatus 1012. The objective lens 1006 is controlled by an objective lens control apparatus 1013. The magnifying lens system 1007 is controlled by a magnifying lens control apparatus 1014. A control mechanism 1005 of the sample holder is controlled by a holder control apparatus 1015 that controls the driving mechanism of the sample holder.

The electron beam 1003 having passed through the sample S is detected by the radiation detector 1100. The output signal from the radiation detector 1100 is processed by a signal processing apparatus 1016 and an image processing apparatus 1018, and an image signal is generated. The generated image (transmission electron image) is displayed on an image display monitor 1020 and an analysis monitor 1021 serving as display apparatuses.

The transmission electron microscope (TEM) system of the present embodiment including the radiation detector according to any one of the first to eighth embodiments enables realizing a transmission electron microscope (TEM) system having excellent reliability and durability and capable of obtaining a captured image of high image quality.

To be noted, the electron microscope according to the embodiments is not limited to the transmission electron microscope (TEM) described as an example, and may be, for example, a scanning electron microscope (SEM) or a scanning transmission electron microscope (STEM). Further, for example, an electron microscope having a processing function such as ion beam milling or ion beam-induced deposition (IBID), or a dual-beam electron microscope including a focused ion beam (FIB) such as FIB-SEM may be used.

Modification of Embodiments

To be noted, the present invention is not limited to the embodiments described above, and can be modified in many ways within the technical concept of the present invention. For example, different embodiments described above may be implemented in combination.

Although a case where the elastic modulus of the first member and the elastic modulus of the second member are different has been mainly described, the present invention is also applicable to a case where a physical property other than the elastic modulus is different. For example, the present invention is also effective in the case where the thermal expansion coefficient of the first member and the thermal expansion coefficient of the second member are different. If the first member and the second member each have a different thermal expansion coefficient, each member contracts differently when the semiconductor layer is cooled by using a cooling device. However, according to the embodiments, since the first member and the third member are coupled via a buffer member and the second member and the third member are coupled via an adhesive layer, excessive force locally acting on the semiconductor layer can be suppressed. Therefore, in a work of attaching a radiation detector to a radiation detection apparatus or the like, damaging of the semiconductor layer can be suppressed, and the workability, reliability, and yield can be improved.

OTHER EMBODIMENTS

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-80621, filed May 17, 2022, and Japanese Patent Application No. 2023-17436, filed Feb. 8, 2023, which are hereby incorporated by reference herein in their entirety.

What is claimed is:
1. A radiation detector comprising:
a semiconductor layer including a light receiving portion configured to receive radiation; and
a cooling device disposed at a distance from the semiconductor layer in a direction perpendicular to a main surface of the semiconductor layer,
wherein a first member and a second member are provided along a plane that is positioned between the semiconductor layer and the cooling device and that is parallel to the main surface of the semiconductor layer, the second member having physical properties different from physical properties of the first member, and
in the direction perpendicular to the main surface of the semiconductor layer, the first member and a third member are coupled via a first buffer member, and the second member and the third member are coupled via an adhesive layer.
2. The radiation detector according to claim 1, wherein an elastic modulus of the first member is higher than an elastic modulus of the second member, and the first buffer member is more easily deformed by an external force than the adhesive layer.
3. The radiation detector according to claim 1, wherein the first buffer member includes any one of a pseudoplastic fluid, a plastic fluid, a double-sided tape, or a die attach film.
4. The radiation detector according to claim 1, wherein the first buffer member is grease.
5. The radiation detector according to claim 1, wherein the second member is provided at a position farther away from the light receiving portion than the first member in a direction along the plane.

6. The radiation detector according to claim 1, wherein a space is provided on a back surface side of the light receiving portion.

7. The radiation detector according to claim 1, wherein the first member is a heat conducting member, the second member is a circuit board, and the third member is the semiconductor layer.

8. The radiation detector according to claim 7, wherein the first member and the cooling device are coupled via a second buffer member.

9. The radiation detector according to claim 8, wherein the second buffer member includes any one of a pseudoplastic fluid, a plastic fluid, a double-sided tape, or a die attach film.

10. The radiation detector according to claim 8, wherein the second buffer member is grease.

11. The radiation detector according to claim 1, wherein the first member is a first heat conducting member, the second member is a circuit board, and the third member is a second heat conducting member.

12. The radiation detector according to claim 11, wherein the third member and the cooling device are coupled via a second buffer member.

13. The radiation detector according to claim 12, wherein the second buffer member includes any one of a pseudo-plastic fluid, a plastic fluid, a double-sided tape, or a die attach film.

14. The radiation detector according to claim 12, wherein the second buffer member is grease.

15. The radiation detector according to claim 11,
wherein a support member is provided between the semi-conductor layer and the first heat conducting member, and
a thermal expansion coefficient of the support member is equal to or higher than a thermal expansion coefficient of the semiconductor layer, and is lower than a thermal expansion coefficient of the first heat conducting member.

16. A radiation imaging system comprising:
the radiation detector according to claim 1; and
a signal processor configured to process a signal output from the radiation detector.

17. A radiation imaging system comprising:
the radiation detector according to claim 1; and
a radiation source.

18. A radiation detection unit comprising:
a semiconductor layer including a light receiving portion configured to receive radiation; and a first heat conducting member disposed at a distance from the semiconductor layer in a direction perpendicular to a main surface of the semiconductor layer,
wherein a first member and a second member are provided along a plane parallel to the main surface of the semiconductor layer, the second member having physical properties different from physical properties of the first member, and
in the direction perpendicular to the main surface of the semiconductor layer, the first member and a third member are coupled via a first buffer member, and the second member and the third member are coupled via an adhesive layer.

19. The radiation detection unit according to claim 18, wherein an elastic modulus of the first member is higher than an elastic modulus of the second member, and the first buffer member is more easily deformed by an external force than the adhesive layer.

20. The radiation detection unit according to claim 18, wherein the first buffer member includes any one of a pseudoplastic fluid, a plastic fluid, a double-sided tape, or a die attach film.

21. The radiation detection unit according to claim 18, wherein the first buffer member is grease.

22. The radiation detection unit according to claim 18, wherein the second member is provided at a position farther away from the light receiving portion than the first member in a direction along the plane.

23. The radiation detection unit according to claim 18, wherein a space is provided on a back surface side of the light receiving portion.

24. The radiation detection unit according to claim 18, wherein the first member is the first heat conducting member, the second member is a circuit board, and the third member is the semiconductor layer.

25. The radiation detection unit according to claim 18, wherein the first member is the first heat conducting member, the second member is a circuit board, and the third member is a second heat conducting member.

26. The radiation detection unit according to claim 18,
wherein a support member is provided between the semi-conductor layer and the first heat conducting member, and
a thermal expansion coefficient of the support member is equal to or higher than a thermal expansion coefficient of the semiconductor layer, and is lower than a thermal expansion coefficient of the first heat conducting member.

* * * * *